US011140486B2

(12) United States Patent
Bae et al.

(10) Patent No.: US 11,140,486 B2
(45) Date of Patent: Oct. 5, 2021

(54) ELECTRONIC DEVICE OPERATING IN ASSOCIATED STATE WITH EXTERNAL AUDIO DEVICE BASED ON BIOMETRIC INFORMATION AND METHOD THEREFOR

(71) Applicant: Samsung Electronics Co., Ltd., Suwon-si (KR)

(72) Inventors: Minho Bae, Suwon-si (KR); Moonsoo Kim, Suwon-si (KR); Hochul Hwang, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 16/922,362

(22) Filed: Jul. 7, 2020

(65) Prior Publication Data
US 2020/0336835 A1 Oct. 22, 2020

Related U.S. Application Data

(63) Continuation of application No. 16/201,473, filed on Nov. 27, 2018, now abandoned.

(30) Foreign Application Priority Data

Nov. 28, 2017 (KR) .......................... 10-2017-0160311

(51) Int. Cl.
*H04R 5/04* (2006.01)
*H04R 1/10* (2006.01)
(Continued)

(52) U.S. Cl.
CPC ............. *H04R 5/04* (2013.01); *A61B 5/6817* (2013.01); *G06F 21/32* (2013.01); *G06F 21/44* (2013.01);
(Continued)

(58) Field of Classification Search
CPC .... H04R 5/04; H04R 1/1041; H04R 2420/01; H04R 2420/07; H04R 2430/01;
(Continued)

(56) References Cited

U.S. PATENT DOCUMENTS 8,325,935 B2 12/2012 Rutschman
8,542,845 B2 9/2013 Cho
(Continued)

FOREIGN PATENT DOCUMENTS

| JP | 2004-120313 A | 4/2004 |
| JP | 2010-529754 A | 8/2010 |

(Continued)

OTHER PUBLICATIONS

International Search Report dated Feb. 27, 2019, issued in International Application No. PCT/KR2018/014746.
(Continued)

*Primary Examiner* — Jason R Kurr
(74) *Attorney, Agent, or Firm* — Jefferson IP Law, LLP

(57) ABSTRACT

An audio output device is provided. The audio output device determines a similarity between a first external subject and a second external subject based on first biometric information about the first external object associated with the audio output device and second biometric information about the second external object associated with an external audio output device, and controls the audio output device and the external audio output device to operation in coordination or independently based on the similarity.

20 Claims, 16 Drawing Sheets

(51) Int. Cl.
*A61B 5/00* (2006.01)
*G06F 21/32* (2013.01)
*H04M 1/60* (2006.01)
*G06F 21/44* (2013.01)
*H04M 1/72412* (2021.01)
*H04M 1/72442* (2021.01)
*A61B 5/021* (2006.01)
*A61B 5/145* (2006.01)
*A61B 5/024* (2006.01)
*A61B 5/389* (2021.01)
*H04M 1/72454* (2021.01)

(52) U.S. Cl.
CPC ..... *H04M 1/6066* (2013.01); *H04M 1/72412* (2021.01); *H04M 1/72442* (2021.01); *H04R 1/1041* (2013.01); *A61B 5/021* (2013.01); *A61B 5/024* (2013.01); *A61B 5/14532* (2013.01); *A61B 5/389* (2021.01); *A61B 5/6898* (2013.01); *H04M 1/6016* (2013.01); *H04M 1/72454* (2021.01); *H04R 2420/01* (2013.01); *H04R 2420/07* (2013.01); *H04R 2430/01* (2013.01)

(58) Field of Classification Search
CPC ......... H04M 1/72412; H04M 1/72442; H04M 1/6066; H04M 1/724454; H04M 1/6016; A61B 5/6817; A61B 5/389; A61B 5/021; A61B 5/024; A61B 5/14532; A61B 5/6898; G06F 21/32; G06F 21/44
See application file for complete search history.

(56) References Cited

U.S. PATENT DOCUMENTS

| | | | |
|---|---|---|---|
| 9,314,172 | B2 | 4/2016 | Wisbey et al. |
| 9,526,947 | B2 | 12/2016 | Wisbey et al. |
| 9,622,685 | B2 | 4/2017 | Wisbey et al. |
| 9,626,478 | B2 | 4/2017 | Armstrong |
| 9,848,828 | B2 | 12/2017 | Wisbey et al. |
| 9,864,843 | B2 | 1/2018 | Wisbey et al. |
| 9,883,278 | B1 * | 1/2018 | Lin .................. H04R 5/033 |
| 10,078,734 | B2 | 9/2018 | Wisbey et al. |
| 10,453,450 | B2 | 10/2019 | Boesen et al. |
| 2006/0251277 | A1 | 11/2006 | Cho |
| 2007/0223725 | A1 | 9/2007 | Neumann et al. |
| 2008/0226094 | A1 | 9/2008 | Rutschman |
| 2008/0298606 | A1 | 12/2008 | Johnson et al. |
| 2009/0023417 | A1 | 1/2009 | Davis et al. |
| 2010/0183175 | A1 | 7/2010 | Chen et al. |
| 2013/0279724 | A1 | 10/2013 | Stafford et al. |
| 2015/0116117 | A1 | 4/2015 | Wisbey et al. |
| 2015/0116125 | A1 | 4/2015 | Armstrong et al. |
| 2015/0116331 | A1 | 4/2015 | Armstrong |
| 2015/0118665 | A1 | 4/2015 | Armstrong |
| 2015/0118669 | A1 | 4/2015 | Wisbey et al. |
| 2015/0119198 | A1 | 4/2015 | Wisbey et al. |
| 2015/0119732 | A1 | 4/2015 | Wisbey et al. |
| 2015/0119760 | A1 | 4/2015 | Wisbey et al. |
| 2015/0120017 | A1 | 4/2015 | Wisbey et al. |
| 2015/0120018 | A1 | 4/2015 | Wisbey et al. |
| 2015/0120019 | A1 | 4/2015 | Wisbey et al. |
| 2015/0120020 | A1 | 4/2015 | Armstrong |
| 2015/0120025 | A1 | 4/2015 | Wisbey et al. |
| 2015/0120202 | A1 | 4/2015 | Armstrong |
| 2015/0120203 | A1 | 4/2015 | Wisbey et al. |
| 2015/0326969 | A1 | 11/2015 | Tu et al. |
| 2016/0007933 | A1 | 1/2016 | Duddy et al. |
| 2016/0022200 | A1 | 1/2016 | Wisbey et al. |
| 2016/0023047 | A1 | 1/2016 | Wisbey et al. |
| 2016/0026215 | A1 | 1/2016 | Armstrong |
| 2016/0026856 | A1 | 1/2016 | Wisbey et al. |
| 2016/0027324 | A1 | 1/2016 | Wisbey et al. |
| 2016/0029125 | A1 | 1/2016 | Armstrong et al. |
| 2016/0029974 | A1 | 2/2016 | Armstrong et al. |
| 2016/0030809 | A1 | 2/2016 | Wisbey et al. |
| 2016/0051184 | A1 | 2/2016 | Wisbey et al. |
| 2016/0051185 | A1 | 2/2016 | Wisbey et al. |
| 2016/0058378 | A1 | 3/2016 | Wisbey et al. |
| 2016/0144237 | A1 | 5/2016 | Wisbey et al. |
| 2016/0210111 | A1 | 7/2016 | Kraft |
| 2017/0013360 | A1 | 1/2017 | Hviid |
| 2017/0049335 | A1 | 2/2017 | Duddy |
| 2017/0105679 | A1 | 4/2017 | Gil |
| 2017/0110124 | A1 | 4/2017 | Boesen et al. |
| 2017/0164089 | A1 | 6/2017 | Lee et al. |
| 2017/0180897 | A1 | 6/2017 | Perianu |
| 2017/0264987 | A1 * | 9/2017 | Hong .................. H04R 1/1025 |
| 2018/0279038 | A1 * | 9/2018 | Boesen ................ H04R 1/1016 |

FOREIGN PATENT DOCUMENTS

| | | |
|---|---|---|
| KR | 10-0617576 B1 | 9/2006 |
| KR | 10-2006-0110064 A | 10/2006 |
| KR | 10-2010-0015531 A | 2/2010 |
| KR | 10-2017-0067050 A | 6/2017 |
| WO | 2015/110587 A1 | 7/2015 |
| WO | 2017/068004 A1 | 4/2017 |
| WO | 2017068000 A1 | 4/2017 |

OTHER PUBLICATIONS

Korean Notice of Allowance dated Sep. 24, 2019, issued in Korean Application No. 10-2017-0160311.

* cited by examiner

ELECTRONIC DEVICE OPERATING IN ASSOCIATED STATE WITH EXTERNAL AUDIO DEVICE BASED ON BIOMETRIC INFORMATION AND METHOD THEREFOR

CROSS-REFERENCE TO RELATED APPLICATION(S)

This application is a continuation application of prior application Ser. No. 16/201,473, filed on Nov. 27, 2018, which claimed priority under 35 U.S.C. § 119(a) of a Korean patent application number 10-2017-0160311, filed on Nov. 28, 2017, in the Korean Intellectual Property Office, the disclosure of which is incorporated by reference herein its entirety.

BACKGROUND

1. Field

The disclosure relates to an audio output device and a control method therefor.

2. Description of Related Art

As electronic communication industries develop, an electronic device with high mobility and accessibility is being developed. For example, a portable electronic device such as a wearable device is being widely used. Also, as the portable electronic device is supplied, methods for monitoring a user state by using the portable electronic device are being developed. For example, a user state may be monitored through a wireless audio output device (e.g., a wireless earphone(s) or a wireless headset) which may be mounted on (or in) user's ear. For example, advanced user experience may be provided by controlling an audio output based on user's state. Accordingly, a method which may control a wireless audio output device based on information about user's state is required.

The above information is presented as background information only to assist with an understanding of the disclosure. No determination has been made, and no assertion is made, as to whether any of the above might be applicable as prior art with regard to the disclosure.

SUMMARY

An audio output device may include a pair of output devices. For example, the pair of output devices may be worn by different users. Also, the pair of output devices may be interconnected wirelessly. In this case, the different users may want to listen to different music. However, the pair of output devices provides the same music as one device, thereby causing degradation of the user experience.

Aspects of the disclosure are to address at least the above-mentioned problems and/or disadvantages and to provide at least the advantages described below. Accordingly, an aspect of the disclosure is to provide a user information-based wireless audio output device which may coincide with a user situation and a control method therefor.

Additional aspects will be set forth in part in the description which follows and, in part, will be apparent from the description, or may be learned by practice of the presented embodiments.

In accordance with an aspect of the disclosure, an audio output device is provided. The audio output device includes at least one communication circuit configured to communicate with an external audio output device, at least one sensor, and at least one processor configured to obtain first biometric information about a first external object associated with the audio output device by using the at least one sensor, obtain second biometric information about a second external object associated with the external audio output device from the external audio output device by using the at least one communication circuit, determine a similarity between the first external object and the second external object based at least on the first biometric information and the second biometric information, operate in coordination with the external audio output device when the similarity satisfies a first specified condition, and operate independently of the external audio output device when the similarity satisfies a second specified condition.

In accordance with another aspect of the disclosure, an electronic device is provided. The electronic device includes at least one communication circuit that communicates with a first external audio output device, a display, and at least one processor configured to receive first biometric information about a first external object associated with the first external audio output device and second biometric information about a second external object associated with a second external audio output device communicating with the first external audio output device from the first external audio output device, by using the at least one communication circuit, determine a similarity between the first external object and the second external object based at least on the first biometric information and the second biometric information, set the first external audio output device such that the first external audio output device operates in coordination with the second external audio output device, when the similarity satisfies a first specified condition, and set the first external audio output device to operate independently of the second external audio output device, when the similarity satisfies a second specified condition.

In accordance with yet another aspect of the disclosure, an electronic device is provided. The electronic device includes at least one communication circuit that communicates with a first external audio output device and a second external audio output device, a display, and at least one processor configured to obtain first biometric information about a first external object associated with the first external audio output device and second biometric information about a second external object associated with the second external audio output device, by using the at least one communication circuit, determine a similarity between the first external object and the second external object based at least on the first biometric information and the second biometric information, set the first external audio output device and the second external audio output device such that the first external audio output device and the second external audio output device operate in coordination with each other, when the similarity satisfies a first specified condition, and to set the first external audio output device and the second external audio output device to operate independently of each other, when the similarity satisfies a second specified condition.

According to embodiments of the disclosure, user's convenience may be improved by controlling a pair of audio output devices independently based on obtained information.

Also, according to various embodiments, an independent control of the pair of audio output devices may be implemented through individual user interfaces for a plurality of users.

Besides, a variety of effects directly or indirectly understood through this disclosure may be provided.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, like reference numerals will be understood to refer to like parts, components, and structures.

DETAILED DESCRIPTION

Figure 1:
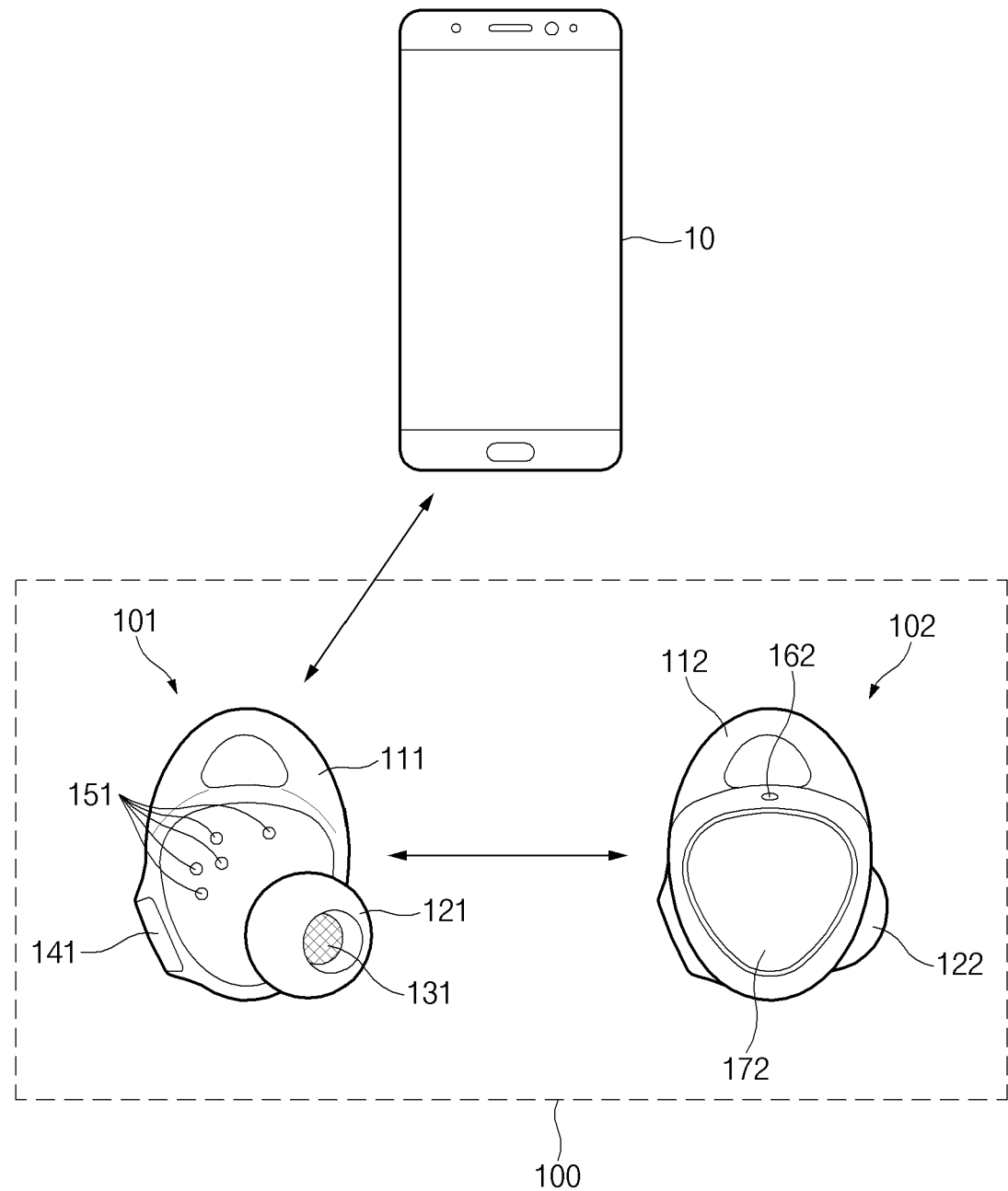
FIG. 1 illustrates an operating environment of an output device according to an embodiment of the disclosure.

The following description with reference to accompanying drawings. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

The terms of a singular form may include plural forms unless otherwise specified. In the disclosure, the expressions "A or B", "at least one of A or/and B", or the like may include any and all combinations of one or more of the associated listed items. The terms, such as "first", "second", and the like may be used to refer to various components regardless of the order and/or the priority and to distinguish the relevant components from other components, but do not limit the components. It will be understood that when a component (e.g., a first component) is referred to as being "(operatively or communicatively) coupled with/to" or "connected to" another component (e.g., a second component), it may be directly coupled with/to or connected to the other component or an intervening component (e.g., a third component) may be present.

According to the situation, the expression "configured to" used in the disclosure may be interchangeably used as, for example, the expression "suitable for", "having the capacity to", "designed to", "adapted to", "made to", or "capable of" in terms of hardware or software. In a situation, the expression "a device configured to" may mean that the device is "capable of" operating together with another device or other parts. For example, a "processor configured to (or set to) perform A, B, and C" may mean a dedicated processor (e.g., an embedded processor) for performing a corresponding operation or a generic-purpose processor (e.g., a central processing unit (CPU) or an application processor) which performs corresponding operations by executing one or more software programs which are stored in a memory device.

An electronic device according to various embodiments of the disclosure may include at least one of, for example, smartphones, tablet personal computers (PCs), mobile phones, video telephones, electronic book readers, desktop PCs, laptop PCs, netbook computers, workstations, servers, personal digital assistants (PDAs), portable multimedia players (PMPs), motion picture experts group (MPEG-1 or MPEG-2) audio layer 3 (MP3) players, medical devices, cameras, or wearable devices. The wearable device may include at least one of an accessory type (e.g., watches, rings, bracelets, anklets, necklaces, glasses, contact lens, or head-mounted-devices (HMDs), a fabric or garment-integrated type (e.g., an electronic apparel), a body-attached type (e.g., a skin pad or tattoos), or a bio-implantable type (e.g., an implantable circuit). According to various embodiments, the electronic device may include at least one of, for example, televisions (TVs), digital versatile disc (DVD) players, audios, refrigerators, air conditioners, cleaners, ovens, microwave ovens, washing machines, air cleaners, set-top boxes, home automation control panels, security control panels, media box (e.g., Samsung HomeSync™, Apple TV™, or Google TV™), game consoles (e.g., Xbox™ or PlayStation™), electronic dictionaries, electronic keys, camcorders, electronic picture frames, and the like.

According to another embodiment, an electronic device may include at least one of various medical devices (e.g., various portable medical measurement devices (e.g., a blood glucose monitoring device, a heartbeat measuring device, a blood pressure measuring device, a body temperature measuring device, and the like), a magnetic resonance angiography (MRA), a magnetic resonance imaging (MRI), a computed tomography (CT), scanners, and ultrasonic devices), navigation devices, global navigation satellite system (GNSS), event data recorders (EDRs), flight data recorders (FDRs), vehicle infotainment devices, electronic equipment for vessels (e.g., navigation systems for vessels and gyrocompasses), avionics, security devices, head units for vehicles, industrial or home robots, drones, automated teller machines (ATMs), points of sales (POSs) of stores, or internet of things (e.g., light bulbs, various sensors, sprinkler devices, fire alarms, thermostats, street lamps, toasters, exercise equipment, hot water tanks, heaters, boilers, and the like). According to an embodiment, the electronic device may include at least one of parts of furniture, buildings/structures, or a vehicle, electronic boards, electronic signature receiving devices, projectors, or various measuring instruments (e.g., water meters, electricity meters, gas meters, or wave meters, and the like). According to various embodiments, the electronic device may be a flexible one or a combination of two or more of the above-described devices. An electronic device according to an embodiment of the disclosure may not be limited to the above-described electronic devices. In the disclosure, the term "user" may refer to a person who uses an electronic device or may refer to a device (e.g., an artificial intelligence electronic device) that uses the electronic device.

FIG. 1 illustrates an operating environment of an output device according to an embodiment of the disclosure.

Referring to FIG. 1, an audio output device 100 may include a first output device 101 and a second output device 102. For example, the first output device 101 may be mounted on one ear of a user, and the second output device 102 may be mounted on the other ear of the user. In an embodiment, the first output device 101 may communicate with an external electronic device 10 and the second output device 102. The audio output device 100 may operate in association with the external electronic device 10, and may operate standalone.

According to an embodiment, the external electronic device 10 may be one of various mobile devices such as a smartphone, a tablet personal computer (PC), a smart watch, or the like. The external electronic device 10, for example, may output a voice received from any other electronic device during a phone call, a sound source stored in the external electronic device 10 or a sound source being streamed in real time through a communication network, a sound generated upon playing at least one content, or the like. In an embodiment, the voice or the sound source may be transmitted to the audio output device 100, and may be output by the audio output device 100. The audio output device 100 may include the first output device 101 and the second output device 102. The first output device 101 and the second output device 102 are illustrated in FIG. 1 as being kernel-type earphones, but a type of the first output device 101 and the second output device 102 is not limited thereto. For example, the first output device 101 and the second output device 102 may be open-type earphones. Below, a configuration of the first output device 101 will be described with reference to FIG. 1.

According to an embodiment, the first output device 101 may include a wingtip 111, an ear tip 121, a speaker 131, a heart rate (HR) sensor 141, and a terminal 151. The wingtip 111 may be coupled on the periphery of the first output device 101 so as to be replaceable. For example, the wingtip 111 may have elasticity, and may help the first output device 101 to be closely mounted on user's ear. The wingtip 111 may form the exterior of the first output device 101. The ear tip 121 may be coupled at one end of the first output device 101. The ear tip 121 may be, for example, a cylindrical shape. The ear tip 121 may have elasticity, and may help the first output device 101 to be closely mounted on user's ear. The speaker 131 may be positioned within a housing of the first output device 101. The sound output by the speaker 131 may be transferred to user's eardrum through a hollow of a tip. The HR sensor 141 may be positioned within the housing of the first output device 101. When the first output device 101 is mounted on user's ear, the HR sensor 141 may measure a heartbeat of the user by using at least one light emitting unit which may output a light in a specified wavelength range. For example, the at least one light emitting unit may include at least one of an infrared (IR) light emitting unit, a red light emitting unit, a green light emitting unit, a blue light emitting unit, or a white light emitting unit. The first output device 101 may determine whether the first output device 101 is worn by the user, based on the data measured by the HR sensor 141. The terminal 151 may be electrically connected with a charging device, and a battery (not illustrated) of the first output device 101 may be charged through the terminal 151.

The configuration of the first output device 101 illustrated in FIG. 1 is exemplary, and at least a part of the first output device 101 having the configuration illustrated in FIG. 1 may be omitted or replaced. As described above, according to an embodiment, the first output device 101 may be an open earphone. For example, the first output device 101 may not include the wingtip 111. For another example, the first output device 101 may include a speaker, at least a portion of which is exposed, on one surface of the first output device 101 instead of the ear tip 121.

According to an embodiment, the first output device 101 may be wirelessly connected with the external electronic device 10. The first output device 101 may be connected with the external electronic device 10 by wireless communication (e.g., Bluetooth or Bluetooth low energy (BLE)). The first output device 101 may be connected with the external electronic device 10 through a hands-free profile (HFP) or an advanced audio distribution profile (A2DP). In the case where the first output device 101 is connected with the external electronic device 10 through the HFP, the external electronic device 10 may be set to an HFP audio gateway (AG), and the first output device 101 may be set to an HFP hands-free unit (HF). In the case where the first output device 101 is connected with the external electronic device 10 through the A2DP, the external electronic device 10 may be set to an A2DP source (SRC), and the first output device 101 may be set to an A2DP sink (SNK).

According to an embodiment, the first output device 101 may be wirelessly connected with the second output device 102. The first output device 101 may be connected with the second output device 102 by wireless communication (e.g., Bluetooth or BLE). For example, the first output device 101 may be connected with the second output device 102 through the HFP or A2DP. In this case, the first output device 101 may operate as a master, and the second output device 102 may operate as a slave. An example is illustrated in FIG. 1 as the first output device 101 operates as a master and the second output device 102 operates as a slave, but the disclosure is not limited thereto. For example, the second output device 102 may operate as a master, and the first output device 101 may operate as a slave. According to an embodiment, each of the first output device 101 and the second output device 102 may operate as a master. For example, the first output device 101 and the second output device 102 may operate independently of each other. The first output device 101 and the second output device 102 may operate independently of the external electronic device 10.

According to an embodiment, the first output device 101 may be wirelessly connected with the second output device 102. When connected with the external electronic device 10, the first output device 101 may receive audio data associated with a voice or a sound source. The first output device 101 may receive the audio data in a streaming manner and may output the received audio data through the speaker 131. The first output device 101 may transmit the received audio data to the second output device 102. The first output device 101 may output a sound source stored in the first output device 101 or the second output device 102. In this case, the first output device 101 may not be connected with the external electronic device 10. According to an embodiment, the second output device 102 may include a wingtip 112, an ear tip 122, a microphone hole 162, and a touch pad 172. The wingtip 112 and the ear tip 122 of the second output device 102 may be identical to the wingtip 111 and the ear tip 121 of the first output device 101. Although not illustrated in FIG. 1, the second output device 102 may include a speaker, an HR sensor, and a terminal which are identical to those of the first output device 101. Also, although not illustrated in FIG. 1, the first output device 101 may include a microphone hole and a touch pad which are identical to those of the second output device 102.

According to an embodiment, the microphone hole 162 may be formed at a housing of the second output device 102. A microphone may be positioned below the microphone hole 162, and a sound may be transferred to the microphone through the microphone hole 162 from the outside.

According to an embodiment, the touch pad 172 may be formed at a location where the touch pad 172 is exposed when the second output device 102 is inserted into user's ear. The touch pad 172 may sense a contact of user's body. When a touch input is sensed by the touch pad 172, for example, the second output device 102 may perform a function, which corresponds to the touch input, such as play, stop, fast-forward, rewind, volume control, call connection, call end, or the like.

According to various embodiments, the external electronic device 10 may obtain data which are sensed by sensors included in the first output device 101 and the second output device 102. For example, the external electronic device 10 may obtain data sensed by the first output device 101 and data sensed by the second output device 102 through the first output device 101. For another example, the external electronic device 10 may obtain data from each of the first output device 101 and the second output device 102.

According to an embodiment, the external electronic device 10 may identify objects associated with the first output device 101 and the second output device 102, based on a result of comparing the obtained data. For example, the external electronic device 10 may determine whether a first object (e.g., a user which utilizes the first output device 101) and a second object (e.g., a user which utilizes the second output device 102) are different from each other. For example, the external electronic device 10 may determine whether the audio output device 100 is used by a plurality of users. For example, the external electronic device 10 may determine whether the audio output device 100 is used by a plurality of users, by comparing data sensed by the first output device 101 and data sensed by the second output device 102.

According to an embodiment, the external electronic device 10 may control the audio output device 100 based on the data sensed by the first output device 101 and the second output device 102. For example, the external electronic device 10 may control the first output device 101 and the second output device 102 in an associated state or in an independent state. For example, when it is determined that the first object associated with the first output device 101 and the second object associated with the second output device 102 are different from each other, the external electronic device 10 may control the first output device 101 and the second output device 102 so as to operate independently of each other. For another example, when it is determined that the audio output device 100 is used by a plurality of users, the external electronic device 10 may allow the first output device 101 and the second output device 102 to operate independently of each other.

According to an embodiment, the external electronic device 10 may control the audio output device 100 through communication with the audio output device 100. For example, the external electronic device 10 may control the first output device 101 and the second output device 102 by transmitting a signal to the first output device 101 or the second output device 102. In this case, the external electronic device 10 may transmit a signal to a master device of the audio output device 100. For another example, the external electronic device 10 may control the first output device 101 and the second output device 102 by transmitting a signal to the first output device 101 and the second output device 102. In this case, each of the first output device 101 and the second output device 102 may operate as a master device.

According to an embodiment, the external electronic device 10 may set a state of the audio output device 100 through communication with the audio output device 100. For example, the external electronic device 10 may control states of the first output device 101 and the second output device 102 by transmitting a signal to the first output device 101 or the second output device 102. In this case, the external electronic device 10 may transmit a signal to a master device of the audio output device 100. For another example, the external electronic device 10 may control states of the first output device 101 and the second output device 102 by transmitting a signal to the first output device 101 and the second output device 102. In this case, each of the first output device 101 and the second output device 102 may operate as a master device.

According to an embodiment, depending on an operation state of the audio output device 100, the external electronic device 10 may provide information about operation states of the first output device 101 and the second output device 102 or a user interface for controlling the first output device 101 and the second output device 102. For example, when it is determined that the first object associated with the first output device 101 and the second object associated with the second output device 102 are different from each other or when it is determined that the audio output device 100 is used by a plurality of users, the external electronic device 10 may provide, on a display, user interfaces which may control the first output device 101 and the second output device 102 individually. According to an embodiment, the first output device 101 and the second output device 102 may be associated with different applications. For example, the external electronic device 10 may display, on the display, a user interface corresponding to an application associated with the first output device 101 and a user interface corresponding to an application associated with the second output device 102.

According to an embodiment, based at least on information sensed by the first output device 101 and the second output device 102, the external electronic device 10 may set the first output device 101 or the second output device 102 to a master device and may set the other device to a slave device. Also, the external electronic device 10 may provide a notification to the master device. For example, the notification may be associated with a call or a message to the external electronic device 10. For another example, the notification may be associated with an operation state of the audio output device 100.

According to various embodiments, at least a part of the above-described operations of the external electronic device 10 may be performed by the first output device 101. For example, the first output device 101 may obtain data which are sensed by sensors included in the first output device 101 and the second output device 102. For example, the first output device 101 may identify objects associated with the first output device 101 and the second output device 102, by comparing data sensed by the first output device 101 and data sensed by the second output device 102. For example, the first output device 101 may determine whether a first object (e.g., a user which utilizes the first output device 101) and a second object (e.g., a user which utilizes the second output device 102) are different from each other. For example, the first output device 101 may determine whether the audio output device 100 is used by a plurality of users. For example, the first output device 101 may determine whether the audio output device 100 is used by a plurality of users, by comparing data sensed by the first output device 101 and data sensed by the second output device 102. According to an embodiment, the first output device 101 may control the audio output device 100 based on the data sensed by the first output device 101 and the second output device 102. For example, the first output device 101 may control the first output device 101 and the second output device 102 so as to operate in an associated state or in an independent state. Also, the above-described operations may be performed by the second output device 102. Below, exemplary embodiments will be more fully described with reference to FIGS. 2 to 13.

Figure 2:
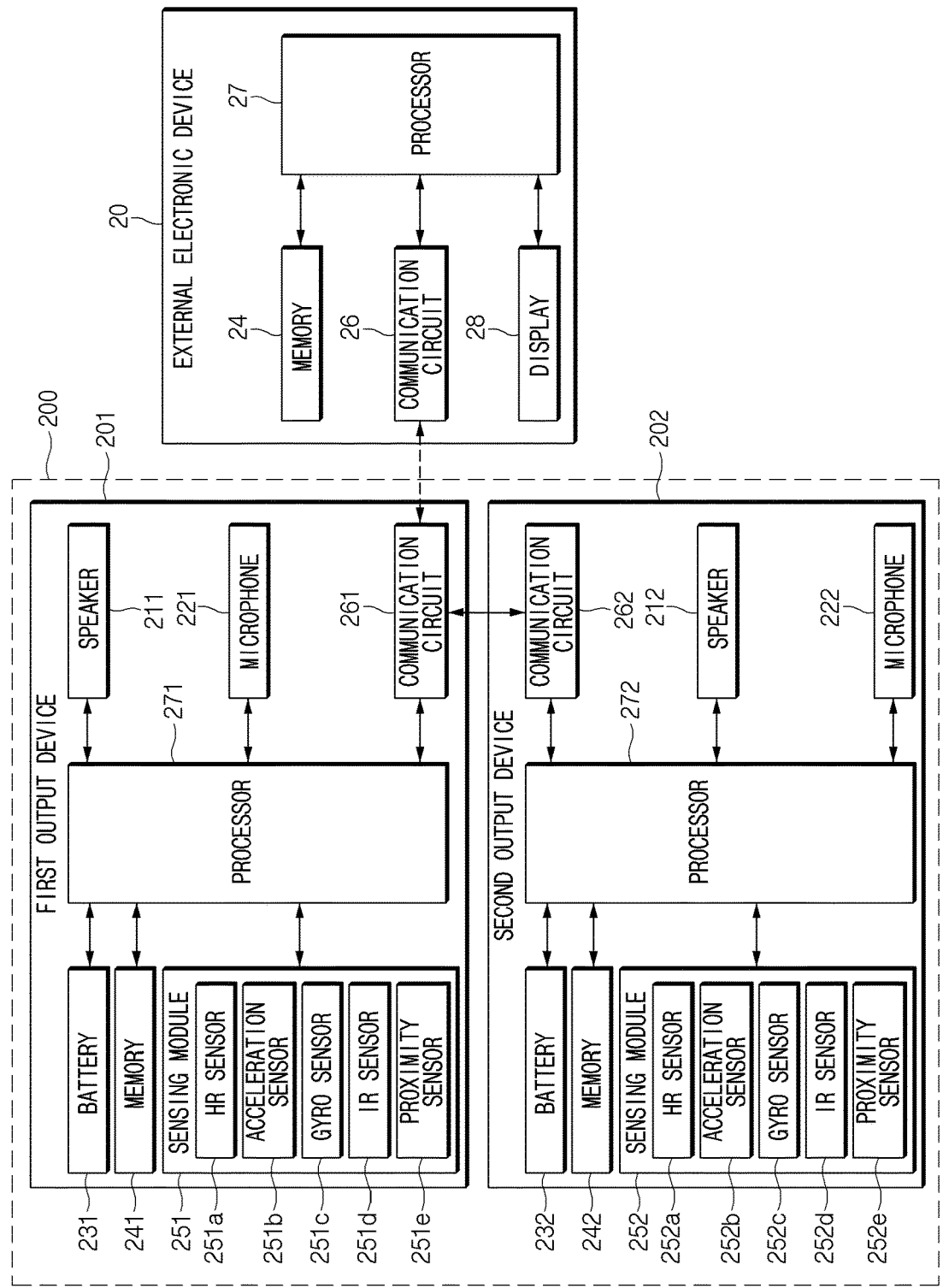
FIG. 2 is a block diagram illustrating a configuration of an audio output device and an external electronic device according to an embodiment of the disclosure.

FIG. 2 is a block diagram illustrating a configuration of an audio output device and an external electronic device according to an embodiment of the disclosure.

Referring to FIG. 2, an audio output device 200 may include a first output device 201 and a second output device 202. The first output device 201 may include a speaker 211, a microphone 221, a battery 231, a memory 241, a sensing module 251, a communication circuit 261, and a processor 271. For example, the first output device 201 may be the same device as the first output device 101 illustrated in FIG. 1. The audio output device 200 may communicate with an external electronic device 20. The external electronic device 20 is illustrated in FIG. 2 as communicating with the first output device 201, but the disclosure is not limited thereto. For example, the external electronic device 20 may communicate with the second output device 202 or may communicate with the first output device 201 and the second output device 202.

According to an embodiment, the second output device 202 may include a speaker 212, a microphone 222, a battery 232, a memory 242, a sensing module 252, a communication circuit 262, and a processor 272. For example, the second output device 202 may be the same device as the second output device 102 illustrated in FIG. 1. Configurations and functions of the speaker 212, the microphone 222, the memory 242, the sensing module 252, the communication circuit 262, and the processor 272 of the second output device 202 may be identical to configurations and functions of the speaker 211, the microphone 221, the battery 231, the memory 241, the sensing module 251, the communication circuit 261, and the processor 271 of the first output device 201.

Below, for convenience of description, the audio output device 200 will be described with respect to the first output device 201, but embodiments to be described below may also be performed by the second output device 202.

According to an embodiment, the speaker 211 may output a sound. The speaker 211 may convert audio data to a sound. In the case where the first output device 201 is inserted into user's ear, the sound output by the speaker 211 may be transferred to user's eardrum.

According to an embodiment, the microphone 221 may sense a sound generated on the outside. For example, the microphone 221 may sense a voice of the user. For another example, the microphone 221 may sense a sound generated around the first output device 201. The sound sensed by the microphone 221 with regard to an ambient environment may be output by the speaker 211.

According to an embodiment, the battery 231 may supply a power to any other components of the first output device 201. The battery 231 may be electrically connected with a power management integrated circuit (PMIC) (not illustrated). In the case where the first output device 201 is connected with a charging device, the battery 231 may be charged wired or wirelessly through the PMIC. The level of the battery 231 may be verified by the PMIC.

According to an embodiment, the memory 241 may store data associated with the first output device 201 and/or the second output device 202. For example, the memory 241 may store a sound source which may be played by the first output device 201 and/or the second output device 202. For another example, the memory 241 may store data sensed by the first output device 201 and/or the second output device 202. For another example, the memory 241 may store data associated with a task which is performed by the first output device 201 and/or the second output device 202.

According to an embodiment, the sensing module 251 may include at least one sensor. The sensing module 251 may sense, for example, a heartbeat, acceleration, an angular velocity, an infrared light, proximity, and/or an electromyogram (EMG). The sensing module 251 may include, for example, an HR sensor 251a, an acceleration sensor 251b, a gyro sensor 251c, an IR sensor 251d, and a proximity sensor 251e. Although not illustrated in FIG. 2, the sensing module 251 may further include various kinds of sensors such as an EMG sensor.

According to an embodiment, the communication circuit 261 may wirelessly communicate with at least one of the external electronic devices 20 or the second output device 202 coupled with the first output device 201. For example, the communication circuit 261 may search for a connectable device around the first output device 201 and may attempt a connection with the found device. The communication circuit 261 may transmit data to the connected device and may receive data from the connected device. The communication circuit 261 may update mutual states with the connected device and may transmit a command to the connected device. The communication circuit 261 may communicate with the external electronic device 20 or the second output device 202 in various manners such as Bluetooth, BLE, Wi-Fi Direct, and/or pronounced ant plus (ANT+).

According to an embodiment, the processor 271 may be electrically connected with the speaker 211, the microphone 221, the battery 231, the memory 241, the sensing module 251, and the communication circuit 261. The processor 271 may control the speaker 211, the microphone 221, the battery 231, the memory 241, the sensing module 251, and the communication circuit 261. The processor 271 may control the second output device 202 and/or the external electronic device 20, which is connected through the communication circuit 261.

According to an embodiment, the processor 271 may obtain data (e.g., a biometric signal) sensed by the sensing module 251 and/or the sensing module 252. For example, the processor 271 may obtain data sensed by the sensing module 252 by using the communication circuit 261. For another example, the processor 271 may obtain information about a state of the sensing module 251 and/or the sensing module 252. For example, the information about the sensing module 251 or 252 may include information about whether each of at least one sensor included in the sensing module 251 or 252 is available.

According to an embodiment, the processor 271 may determine whether the audio output device 200 is used by the same user or by a plurality of users, based on data sensed by the sensing module 251 and/or the sensing module 252. For example, the processor 271 may determine whether the audio output device 200 is used by a plurality of users, based on a result of comparing data sensed by the sensing module 251 and data sensed by the sensing module 252 or based on a similarity between the two data. For another example, when it is determined that the audio output device 200 is used by a plurality of users, the processor 271 may transmit information indicating that the audio output device 200 is used by a plurality of users, to the external electronic device 20.

According to an embodiment, the processor 271 may control the first output device 201 or the second output device 202 based on data sensed by the sensing module 251 and/or the sensing module 252. According to an embodiment, the processor 271 may assign a task to the first output device 201 or the second output device 202 based on data sensed by the sensing module 251 and/or the sensing module 252. Components of the sensing module 252 of the second output device 202 are essentially similar to those of the sensing module 251 of the first output device 201. Thus, the HR sensor 252a, acceleration sensor 252b, gyro sensor 252c, IR sensor 252d, and proximity sensor 252e are substantially similar to the same named components 251x of the sensing module 251. Descriptions thereof will not be repeated for brevity.

According to an embodiment, the processor 271 may obtain information about a wearing state of the audio output device 200, based on data sensed by the sensing module 251 and/or the sensing module 252. In the case where that the first output device 201 and the second output device 202 are used by different users is determined based on the data sensed by the sensing module 251 and/or the sensing module 252, the processor 271 may perform at least one or more additional functions.

For example, in the case where recession from a contacted object is sensed by the proximity sensor 251e, the processor 271 may determine that the first output device 201 is separated from user's ear. For another example, in the case where acceleration (or acceleration of gravity) of a specified magnitude is sensed by the acceleration sensor 251b, the processor 271 may determine that the first output device 201 is separated from user's ear. For another example, in the case where a contact with an external object is sensed by the proximity sensor 251e, the processor 271 may determine that the first output device 201 is mounted on user's ear. For another example, in the case where a heartbeat is sensed by the HR sensor 251a, the processor 271 may determine that the first output device 201 is mounted on user's ear. For another example, in the case where acceleration or angular velocity of a specified magnitude or more is sensed by the acceleration sensor 251b or the gyro sensor 251c, in the case where proximity of an external object is sensed by the proximity sensor 251e, and in the case where a heartbeat is sensed by the HR sensor 251a, the processor 271 may determine that the first output device 201 is mounted on user's ear.

According to an embodiment, the processor 271 may obtain, from the second output device 202, information about a wearing state of the second output device 202 by using the communication circuit 261. For example, the processor 271 may receive data sensed by the sensing module 252 of the second output device 202 from the second output device 202, and may determine a wearing state of the second output device 202 based on the received information. For another example, in the case where the second output device 202 determines a wearing state of the second output device 202 based on data sensed by the sensing module 252 of the second output device 202, the processor 271 may receive a determination result from the second output device 202.

According to an embodiment, in the case where a task is assigned to the first output device 201, the processor 271 may perform the assigned task. The processor 271 may store data associated with the performed task to the memory 241. The processor 271 may transmit the data associated with the performed task to the second output device 202 by using the communication circuit 261.

According to an embodiment, the processor 271 may verify heartbeat information by using the HR sensor 251a of the first output device 201 and an HR sensor 252a of the second output device 202. According to another embodiment, in the case where the first output device 201 and the second output device 202 are mounted on user's ears, the processor 271 may verify heartbeat information. According to another embodiment, the processor 271 may determine whether the audio output device 200 is used by a plurality of users, based at least on first heartbeat information verified from the HR sensor 251a and second heartbeat information verified from the HR sensor 252a. For example, in the case where the similarity between the first heartbeat information and the second heartbeat information is smaller than a specified value or a difference between the first heartbeat information and the second heartbeat information is a specified threshold value or more, the processor 271 may determine that the audio output device 200 is used by a plurality of users. For example, heartbeat information may include at least one of a heart rate, a heartbeat timing, a heartbeat interval, a heartbeat waveform, or a heartbeat frequency.

According to an embodiment, the processor 271 may determine whether the audio output device 200 is used by a plurality of users, based on angular velocities sensed by the acceleration sensor 251b and an acceleration sensor 252b. For example, in the case where a difference between a first acceleration sensed by the acceleration sensor 251b and a second acceleration sensed by the acceleration sensor 252b is a specified value or more, the processor 271 may determine that the audio output device 200 is used by a plurality of users.

According to an embodiment, the processor 271 may determine whether the audio output device 200 is used by a plurality of users, based on a direction of the first output device 201 sensed by the gyro sensor 251*c* and a direction of the second output device 202 sensed by a gyro sensor 252*c*. For example, in the case where a direction (e.g., an output direction of the speaker 211) in which the first output device 201 faces and a direction (e.g., an output direction of the speaker 212) in which the second output device 202 faces face each other, the processor 271 may determine that the audio output device 200 is used by a plurality of users. For another example, in the case where a direction in which the first output device 201 faces and a direction in which the second output device 202 faces are out of a specified range, the processor 271 may determine that the audio output device 200 is used by a plurality of users.

According to an embodiment, the processor 271 may determine whether the audio output device 200 is used by a plurality of users, based on a distance between the first output device 201 and the second output device 202. For example, the processor 271 may determine a distance between the first output device 201 and the second output device 202 by transmitting a specified signal to the second output device 202 by using the communication circuit 261 and receiving a response from the second output device 202. The processor 271 may determine a distance based on a time (e.g., a round trip time) between the transmission of the specified signal and the response. For another example, in the case where the time from the transmission to the response or the distance is a specified value or more, the processor 271 may determine that the first output device 201 and the second output device 202 are used by different users.

According to an embodiment, when it is determined that the first output device 201 and the second output device 202 are used by different users, the processor 271 may assign a task being performed by the first output device 201 to the second output device 202. For example, the processor 271 may transmit data associated with the task being performed by the first output device 201 to the second output device 202 by using the communication circuit 261. For another example, while the first output device 201 and the second output device 202 operate in a stereo mode, when it is determined that the first output device 201 and the second output device 202 are used by different users, the processor 271 may set the first output device 201 and the second output device 202 such that the first output device 201 and the second output device 202 operate in a mono mode.

According to an embodiment, the processor 271 may assign a task to the first output device 201 or the second output device 202 based on a user input. For example, the processor 271 may output a call voice, a notification, or the like through the first output device 201 or the second output device 202 in the mono mode. For another example, the processor 271 may control the first output device 201 and/or the second output device 202 based on a task or a user input such that only one of the first output device 201 or the second output device 202 is used. For another example, the processor 271 may activate or deactivate the microphone 221 of the first output device 201 and/or the microphone 222 of the second output device 202.

According to an embodiment, various embodiments which are above described as being performed by the processor 271 of the first output device 201 may be performed by the processor 272 of the second output device 202. For example, the processor 271 of the first output device 201 may control the processor 272 of the second output device 202 such that the various embodiments described above are performed by the processor 272 of the second output device 202. Below, various embodiments will be described with respect to the external electronic device 20. At least some of the embodiments described above as being performed by the processor 271 may be performed by the external electronic device 20.

According to an embodiment, the external electronic device 20 may include a memory 24, a communication circuit 26, a display 28, and a processor 27. The processor 27 may be electrically connected with the memory 24, the communication circuit 26, and the display 28. According to an embodiment, the processor 27 may control the first output device 201 and/or the second output device 202, which is connected through the communication circuit 26. For example, the external electronic device 20 may be the same device as the external electronic device 10 illustrated in FIG. 1.

According to an embodiment, the memory 24 may store data associated with the first output device 201 and/or the second output device 202. For example, the memory 24 may store a sound source which may be played by the first output device 201 and/or the second output device 202. For another example, the memory 24 may store data sensed by the first output device 201 and/or the second output device 202. For another example, the memory 24 may store data associated with a task which is performed by the first output device 201 and/or the second output device 202.

According to an embodiment, the communication circuit 26 may wirelessly communicate with at least one of the first output device 201 or the second output device 202. For example, the communication circuit 26 may search for a connectable device around the external electronic device 20 and may attempt a connection with the found device. The communication circuit 26 may transmit data to the connected device and may receive data from the connected device. The communication circuit 26 may update mutual states with the connected device and may transmit a command to the connected device. The communication circuit 26 may communicate with the first output device 201 or the second output device 202 in various manners such as Bluetooth, BLE, Wi-Fi Direct, and/or ANT+.

According to an embodiment, the processor 27 may obtain data (e.g., a biometric signal) sensed by the sensing module 251 and/or the sensing module 252. According to an embodiment, by using the communication circuit 26, the processor 27 may obtain data sensed by the sensing module 251 from the first output device 201 and may obtain data sensed by the sensing module 252 from the first output device 201 or the second output device 202. For another example, the processor 27 may obtain information about a state of the sensing module 251 and/or the sensing module 252. For example, the information about the sensing module 251 or 252 may include information about whether each of at least one sensor included in the sensing module 251 or 252 is available.

According to an embodiment, the processor 27 may determine whether the audio output device 200 is used by the same user or by a plurality of users, based on data sensed by the sensing module 251 and/or the sensing module 252. For example, the processor 27 may determine whether the audio output device 200 is used by a plurality of users, based on a result of comparing data sensed by the sensing module 251 and data sensed by the sensing module 252 or based on a similarity between the two data.

According to an embodiment, the processor 27 may control the first output device 201 or the second output device 202 based on data sensed by the sensing module 251 and/or the sensing module 252. According to an embodiment, the processor 27 may assign a task to the first output device 201 or the second output device 202 based on data sensed by the sensing module 251 and/or the sensing module 252.

According to an embodiment, the processor 27 may obtain information about a wearing state of the audio output device 200, based on data sensed by the sensing module 251 and/or the sensing module 252. In the case where that the first output device 201 and the second output device 202 are used by different users is determined based on the data sensed by the sensing module 251 and/or the sensing module 252, the processor 27 may perform at least one or more additional functions. According to another embodiment, the processor 27 may receive information indicating that the first output device 201 and the second output device 202 are used by different users, from the first output device 201 or the second output device 202.

For example, in the case where recession from a contacted object is sensed by the proximity sensor 251e, the processor 27 may determine that the first output device 201 is separated from user's ear. For another example, in the case where acceleration (or acceleration of gravity) of a specified magnitude is sensed by the acceleration sensor 251b, the processor 27 may determine that the first output device 201 is separated from user's ear. For another example, in the case where a contact with an external object is sensed by the proximity sensor 251e, the processor 27 may determine that the first output device 201 is mounted on user's ear. For another example, in the case where a heartbeat is sensed by the HR sensor 251a, the processor 27 may determine that the first output device 201 is mounted on user's ear. For another example, in the case where acceleration or angular velocity of a specified magnitude or more is sensed by the acceleration sensor 251b or the gyro sensor 251c, in the case where proximity of an external object is sensed by the proximity sensor 251e, and in the case where a heartbeat is sensed by the HR sensor 251a, the processor 27 may determine that the first output device 201 is mounted on user's ear. For another example, the processor 27 may receive, from the first output device 201, information about a wearing state of the first output device 201 determined by the first output device 201.

According to an embodiment, the processor 27 may obtain information about a wearing state of the audio output device 200 from the first output device 201 and/or the second output device 202 by using the communication circuit 26. For example, the processor 27 may receive data sensed by the sensing module 252 of the second output device 202 from the first output device 201 or the second output device 202, and may determine a wearing state of the second output device 202 based on the received information. For another example, the processor 27 may receive information about a wearing state determined by the second output device 202 from the first output device 201 or the second output device 202.

According to an embodiment, the processor 27 may verify heartbeat information by using the HR sensor 251a of the first output device 201 and the HR sensor 252a of the second output device 202. According to another embodiment, in the case where the first output device 201 and the second output device 202 are mounted on user's ears, the processor 27 may verify heartbeat information. According to another embodiment, the processor 27 may determine whether the audio output device 200 is used by a plurality of users, based on first heartbeat information verified from the HR sensor 251a and second heartbeat information verified from the HR sensor 252a. For example, in the case where the similarity between the first heartbeat information and the second heartbeat information is smaller than a specified value or a difference between the first heartbeat information and the second heartbeat information is a specified threshold value or more, the processor 27 may determine that the audio output device 200 is used by a plurality of users. For example, heartbeat information may include at least one of a heart rate, a heartbeat timing, a heartbeat interval, a heartbeat waveform, or a heartbeat frequency.

According to an embodiment, when the audio output device 200 is determined as being used by a plurality of users or when information indicating that the audio output device 200 is used by a plurality of users is received from the audio output device 200 (e.g., the first output device 201 or the second output device 202), the processor 27 may display an image indicating the use of the audio output device 200 by a plurality of users on the display 28. For example, the processor 27 may display a pop-up message indicating that the audio output device 200 is used by a plurality of users, on the display 28. For another example, the processor 27 may display an icon indicating that the audio output device 200 is used by a plurality of users, in at least partial area on the display 28.

According to an embodiment, in the case where the audio output device 200 is used by a plurality of users (e.g., in the case where the use of the audio output device 200 by a plurality of users is determined or the use of the audio output device 200 by a plurality of users is received), an input for controlling an output characteristic of the audio output device 200 may be received. For example, the output characteristic of the audio output device 200 may include at least one of an output intensity (e.g., a volume), an output intensity for each frequency band, or an output filter characteristic. For example, the input associated with the control of the output characteristic may include a touch input on the display 28 or an input to a button on the external electronic device 20. For another example, the input for controlling the output characteristic of the audio output device 200 may be received by the external electronic device 20 through the first output device 201 or the second output device 202.

According to an embodiment, in the case where the audio output device 200 is used by a plurality of users and the input for controlling the output characteristic of the audio output device 200 is received, the processor 27 may display a user interface for controlling an output characteristic of each of the first output device 201 and the second output device 202 on the display 28. For example, the input for a volume control of the audio output device 200 may be received. In this case, when the audio output device 200 is used by a plurality of users and an input for a volume control is received, the processor 27 may display a user interface (e.g., a scroll bar) for a volume control of the first output device 201 and a user interface for a volume control of the second output device 202 in at least a portion of the display 28. For another example, an input for controlling an output frequency characteristic of the audio output device 200 may be received. In this case, when the audio output device 200 is used by a plurality of users and an input for controlling the output frequency characteristic is received, the processor 27 may display a user interface (e.g., an equalizer) for controlling an output frequency characteristic of the first output device 201 and a user interface for controlling an output frequency characteristic of the second output device 202 in at least a portion of the display 28.

According to an embodiment, in the case where the audio output device 200 is used by a plurality of users and an input for playing a sound source is received, the processor 27 may display a user interface for playing different sound sources at the first output device 201 and the second output device 202 in at least a portion of the display 28. For example, the processor 27 may display a sound source selection user interface for the first output device 201 and a sound source selection user interface for the second output device 202 in at least a portion of the display 28. For another example, the processor 27 may display a user interface corresponding to a sound source associated with the first output device 201 and a user interface corresponding to a sound source associated with the second output device 202 in at least a portion of the display 28. For another example, the processor 27 may display a user interface associated with the second output device 202 as an image in which the user interface associated with the second output device 202 overlaps at least a portion of a user interface associated with the first output device 201.

According to an embodiment, in the case where the audio output device 200 is used by a plurality of users, the processor 27 may assign a task being performed by the first output device 201 to the second output device 202. For example, the processor 27 may control the first output device 201 to allow the first output device 201 to transmit data associated with a task being performed by the first output device 201 to the second output device 202. For another example, while the first output device 201 and the second output device 202 operate in a stereo mode, when it is determined that the first output device 201 and the second output device 202 are used by different users, the processor 27 may set the first output device 201 and the second output device 202 such that the first output device 201 and the second output device 202 operate in a mono mode.

According to an embodiment, the processor 27 may assign a task to the first output device 201 or the second output device 202 based on a user input. For example, the processor 27 may output a call voice or a notification through the first output device 201 or the second output device 202 in the mono mode. For another example, the processor 27 may control the first output device 201 and/or the second output device 202 based on a task or a user input such that only one of the first output device 201 or the second output device 202 is used. For another example, the processor 27 may activate or deactivate the microphone 221 of the first output device 201 and/or the microphone 222 of the second output device 202.

According to an embodiment, the first output device 201 may include the at least one communication circuit 261, at least one sensor (e.g., the sensing module 251), and a control circuit (e.g., the processor 271). Also, the communication circuit may be configured to obtain first biometric information about a first external object associated with the first output device 201 by using the at least one sensor, to obtain second biometric information about a second external object associated with the second output device 202 from the second output device 202 by using the at least one communication circuit 261, and to determine a similarity between the first external object and the second external object based at least on the first biometric information and the second biometric information. Also, the control circuit may be configured to operate together with the second output device 202 when the similarity satisfies a first specified condition, and to operate independently of the second output device 202 when the similarity satisfies a second specified condition.

According to an embodiment, when the similarity satisfies the first specified condition, the control circuit may be configured to output first audio data through the first output device 201 and to transmit at least a portion of the first audio data to the second output device 202 by using the at least one communication circuit 261.

According to an embodiment, the control circuit may be configured to control the first output device 201 and the second output device 202 so as to have the same audio output characteristic when the similarity satisfies the first specified condition, and to control the first output device 201 and the second output device 202 so as to have different audio output characteristics when the similarity satisfies the second specified condition. For example, the audio output characteristic may include at least one of a volume or a volume for each frequency band.

According to an embodiment, the at least one communication circuit 261 may communicate with the second output device 202 and an external electronic device 20. Also, when the similarity satisfies the second specified condition, the control circuit may be configured to transmit information, which indicates that objects associated with the first output device 201 and the second output device 202 are different, to the external electronic device 20 by using the at least one communication circuit 261.

According to an embodiment, the first biometric information and the second biometric information may include at least one of a heart rate, a heartbeat waveform, a heartbeat timing, or a heartbeat frequency, and the control circuit may be configured to determine a similarity between the first external object and the second external object based on a similarity between the first biometric information and the second biometric information.

According to an embodiment, the external electronic device 20 may include at least one communication circuit 26 communicating with the first output device 201, the display 28, and the processor 27. Also, the processor 27 may be configured to receive first biometric information about a first external object associated with the first output device 201 and second biometric information about a second external object associated with the second output device 202 communicating with the first output device 201 from the first output device 201, by using the at least one communication circuit 26, to determine a similarity between the first external object and the second external object based at least on the first biometric information and the second biometric information, to set the first output device 201 such that the first output device 201 operates together with the second output device 202, when the similarity satisfies a first specified condition, and to set the first output device 201 such that the first output device 201 operates independently of the second output device 202, when the similarity satisfies a second specified condition.

According to an embodiment, the processor 27 may be configured to transmit first audio data to at least one of the first output device 201 and the second output device 202 by using the at least one communication circuit 26, when the similarity satisfies the first specified condition, and to transmit the first audio data to the first output device 201 and second audio data to the second output device 202, by using the at least one communication circuit 26, when the similarity satisfies the second specified condition. For example, the processor 27 may be configured to display a user interface for a control of the first audio data in at least a portion on the display 28, when the similarity satisfies the first specified condition, and to display a user interface for an independent control of the first audio data and the second audio data in the at least a portion on the display 28, when the similarity satisfies the second specified condition. For another example, the processor 27 may be configured to set the first output device 201 and the second output device 202 such that the first output device 201 and the second output device 202 have the same audio output characteristic, when the similarity satisfies the first specified condition, and to set the first output device 201 such that the first output device 201 and the second output device 202 have different audio output characteristics, when the similarity satisfies the second specified condition. The audio output characteristic may include at least one of a volume or a volume for each frequency band. For another example, in the case where a user input for the audio output characteristic control is received, the processor 27 may be configured to display a user interface for an associated control of audio output characteristics of the first output device 201 and the second output device 202 in at least a portion on the display 28, when the similarity satisfies the first specified condition, and to display a user interface for an independent control of the audio output characteristics of the first output device 201 and the second output device 202 in the at least a portion on the display 28, when the similarity satisfies the second specified condition.

According to an embodiment, the processor 27 may be configured to display information, which indicates that the first output device 201 and the second output device 202 are associated with different objects, in at least a portion on the display 28, when the similarity satisfies the second specified condition. For example, the processor 27 may be configured to display at least one of an icon, a character, an image, or a pop-up message on the display as at least a portion of the indicating information.

According to an embodiment, the first biometric information and the second biometric information may include at least one of a heart rate, a heartbeat waveform, a heartbeat timing, or a heartbeat frequency, and the processor 27 may be configured to determine a similarity between the first external object and the second external object based on a similarity between the first biometric information and the second biometric information.

According to an embodiment, the external electronic device 20 may include the at least one communication circuit 26 communicating with a first output device 201 and a second output device 202, the display 28, and the processor 27. Also, the processor 27 may be configured to obtain first biometric information about a first external object associated with the first output device 201 and second biometric information about a second external object associated with the second output device 202, by using the at least one communication circuit 26, to determine a similarity between the first external object and the second external object based at least on the first biometric information and the second biometric information, to set the first output device 201 and the second output device 202 such that the first output device 201 and the second output device 202 operate together, when the similarity satisfies a first specified condition, and to set the first output device 201 and the second output device 202 such that the first output device 201 and the second output device 202 operate independently of each other, when the similarity satisfies a second specified condition.

According to an embodiment, the processor 27 may be configured to transmit first audio data to at least one of the first output device 201 and the second output device 202 by using the at least one communication circuit 26, when the similarity satisfies the first specified condition, and to transmit the first audio data to the first output device 201 and second audio data to the second output device 202, by using the at least one communication circuit 26, when the similarity satisfies the second specified condition.

According to an embodiment, the processor 27 may be configured to display a user interface for a control of the first audio data in at least a portion on the display 28, when the similarity satisfies the first specified condition, and to display a user interface for an independent control of the first audio data and the second audio data in the at least a portion on the display 28, when the similarity satisfies the second specified condition.

According to an embodiment, the processor 27 may be configured to set the first output device 201 and the second output device 202 such that the first output device 201 and the second output device 202 have the same audio output characteristic, when the similarity satisfies the first specified condition, and to set the first output device 201 and the second output device 202 such that the first output device 201 and the second output device 202 have different audio output characteristics, when the similarity satisfies the second specified condition. Also, the audio output characteristic may include at least one of a volume or a volume for each frequency band.

Figure 3:
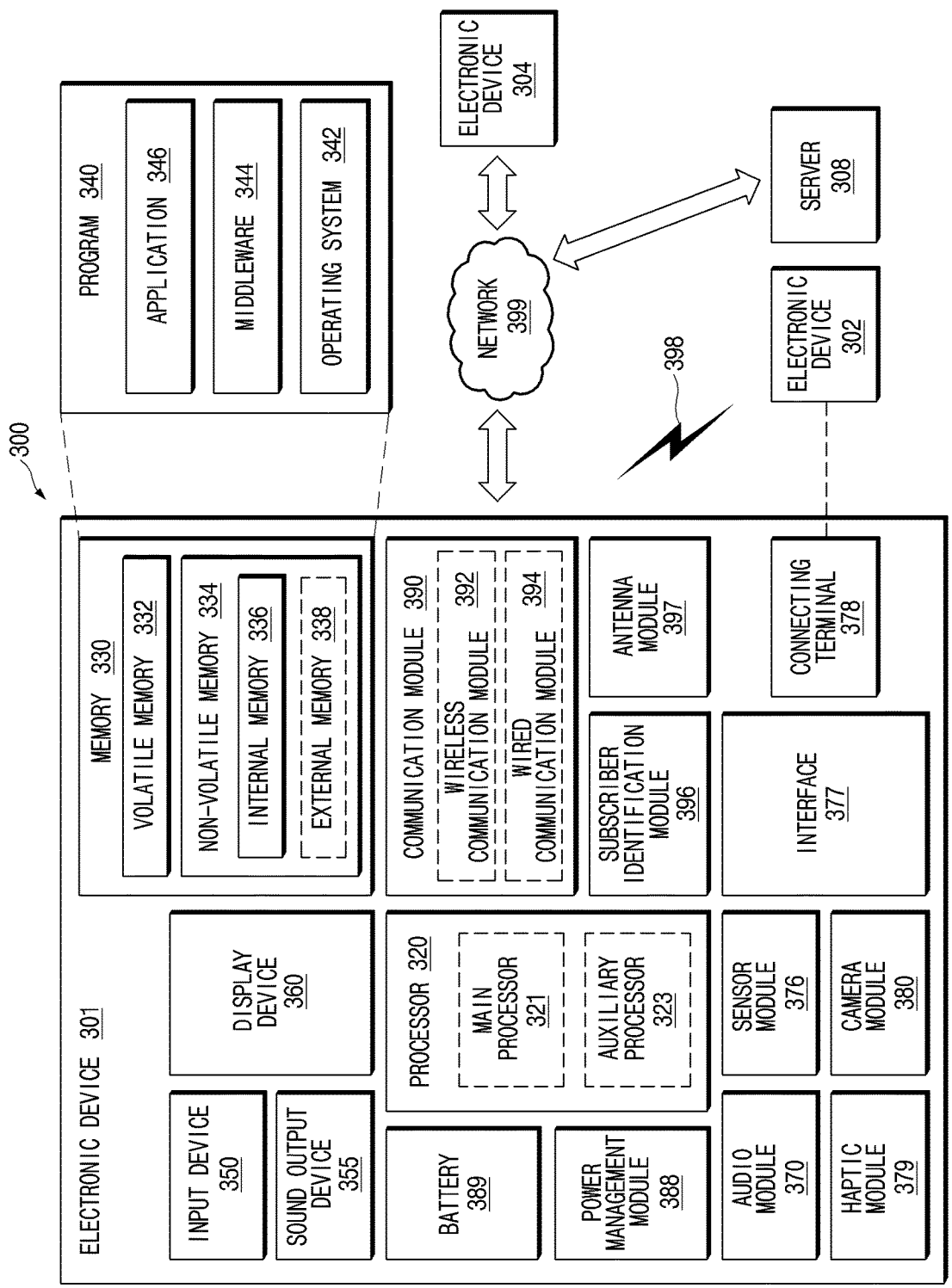
FIG. 3 illustrates an electronic device in a network environment, according to various embodiments of the disclosure.

FIG. 3 is a block diagram illustrating an electronic device 301 in a network environment 300 according to various embodiments.

For example, the electronic device 301 may be the same device as the external electronic device 10 illustrated in FIG. 1. Also, for example, an external electronic device 302 may be the same device as the first output device 101, the second output device 102, or the audio output device 100. Referring to FIG. 3, the electronic device 301 in the network environment 300 may communicate with an electronic device 302 via a first network 398 (e.g., a short-range wireless communication network), or an electronic device 304 or a server 308 via a second network 399 (e.g., a long-range wireless communication network). According to an embodiment, the electronic device 301 may communicate with the electronic device 304 via the server 308. According to an embodiment, the electronic device 301 may include a processor 320, memory 330, an input device 350, a sound output device 355, a display device 360, an audio module 370, a sensor module 376, an interface 377, a haptic module 379, a camera module 380, a power management module 388, a battery 389, a communication module 390, a subscriber identification module (SIM) 396, or an antenna module 397. In some embodiments, at least one (e.g., the display device 360 or the camera module 380) of the components may be omitted from the electronic device 301, or one or more other components may be added in the electronic device 301. In some embodiments, some of the components may be implemented as single integrated circuitry. For example, the sensor module 376 (e.g., a fingerprint sensor, an iris sensor, or an illuminance sensor) may be implemented as embedded in the display device 360 (e.g., a display).

The processor 320 may execute, for example, software (e.g., a program 340) to control at least one other component (e.g., a hardware or software component) of the electronic device 301 coupled with the processor 320, and may perform various data processing or computation. According to one embodiment, as at least part of the data processing or computation, the processor 320 may load a command or data received from another component (e.g., the sensor module 376 or the communication module 390) in volatile memory 332, process the command or the data stored in the volatile memory 332, and store resulting data in non-volatile memory 334. According to an embodiment, the processor 320 may include a main processor 321 (e.g., a central processing unit (CPU) or an application processor (AP)), and an auxiliary processor 323 (e.g., a graphics processing unit (GPU), an image signal processor (ISP), a sensor hub processor, or a communication processor (CP)) that is operable independently from, or in conjunction with, the main processor 321. Additionally or alternatively, the auxiliary processor 323 may be adapted to consume less power than the main processor 321, or to be specific to a specified function. The auxiliary processor 323 may be implemented as separate from, or as part of the main processor 321.

The auxiliary processor 323 may control at least some of functions or states related to at least one component (e.g., the display device 360, the sensor module 376, or the communication module 390) among the components of the electronic device 301, instead of the main processor 321 while the main processor 321 is in an inactive (e.g., sleep) state, or together with the main processor 321 while the main processor 321 is in an active state (e.g., executing an application). According to an embodiment, the auxiliary processor 323 (e.g., an image signal processor or a communication processor) may be implemented as part of another component (e.g., the camera module 380 or the communication module 390) functionally related to the auxiliary processor 323.

The memory 330 may store various data used by at least one component (e.g., the processor 320 or the sensor module 376) of the electronic device 301. The various data may include, for example, software (e.g., the program 340) and input data or output data for a command related thererto. The memory 330 may include the volatile memory 332 or the non-volatile memory 334.

The program 340 may be stored in the memory 330 as software, and may include, for example, an operating system (OS) 342, middleware 344, or an application 346.

The input device 350 may receive a command or data to be used by other component (e.g., the processor 320) of the electronic device 301, from the outside (e.g., a user) of the electronic device 301. The input device 350 may include, for example, a microphone, a mouse, or a keyboard.

The sound output device 355 may output sound signals to the outside of the electronic device 301. The sound output device 355 may include, for example, a speaker or a receiver. The speaker may be used for general purposes, such as playing multimedia or playing record, and the receiver may be used for an incoming call. According to an embodiment, the receiver may be implemented as separate from, or as part of the speaker.

The display device 360 may visually provide information to the outside (e.g., a user) of the electronic device 301. The display device 360 may include, for example, a display, a hologram device, or a projector and control circuitry to control a corresponding one of the display, hologram device, and projector. According to an embodiment, the display device 360 may include touch circuitry adapted to detect a touch, or sensor circuitry (e.g., a pressure sensor) adapted to measure the intensity of force incurred by the touch.

The audio module 370 may convert a sound into an electrical signal and vice versa. According to an embodiment, the audio module 370 may obtain the sound via the input device 350, or output the sound via the sound output device 355 or a headphone of an external electronic device (e.g., an electronic device 302) directly (e.g., wiredly) or wirelessly coupled with the electronic device 301.

The sensor module 376 may detect an operational state (e.g., power or temperature) of the electronic device 301 or an environmental state (e.g., a state of a user) external to the electronic device 301, and then generate an electrical signal or data value corresponding to the detected state. According to an embodiment, the sensor module 376 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 377 may support one or more specified protocols to be used for the electronic device 301 to be coupled with the external electronic device (e.g., the electronic device 302) directly (e.g., wiredly) or wirelessly. According to an embodiment, the interface 377 may include, for example, a high definition multimedia interface (HDMI), a universal serial bus (USB) interface, a secure digital (SD) card interface, or an audio interface.

A connecting terminal 378 may include a connector via which the electronic device 301 may be physically connected with the external electronic device (e.g., the electronic device 302). According to an embodiment, the connecting terminal 378 may include, for example, a HDMI connector, a USB connector, a SD card connector, or an audio connector (e.g., a headphone connector).

The haptic module 379 may convert an electrical signal into a mechanical stimulus (e.g., a vibration or a movement) or electrical stimulus which may be recognized by a user via his tactile sensation or kinesthetic sensation. According to an embodiment, the haptic module 379 may include, for example, a motor, a piezoelectric element, or an electric stimulator.

The camera module 380 may capture a still image or moving images. According to an embodiment, the camera module 380 may include one or more lenses, image sensors, image signal processors, or flashes.

The power management module 388 may manage power supplied to the electronic device 301. According to one embodiment, the power management module 388 may be implemented as at least part of, for example, a power management integrated circuit (PMIC).

The battery 389 may supply power to at least one component of the electronic device 301. According to an embodiment, the battery 389 may include, for example, a primary cell which is not rechargeable, a secondary cell which is rechargeable, or a fuel cell.

The communication module 390 may support establishing a direct (e.g., wired) communication channel or a wireless communication channel between the electronic device 301 and the external electronic device (e.g., the electronic device 302, the electronic device 304, or the server 308) and performing communication via the established communication channel. The communication module 390 may include one or more communication processors that are operable independently from the processor 320 (e.g., the application processor (AP)) and supports a direct (e.g., wired) communication or a wireless communication. According to an embodiment, the communication module 390 may include a wireless communication module 392 (e.g., a cellular communication module, a short-range wireless communication module, or a global navigation satellite system (GNSS) communication module) or a wired communication module 394 (e.g., a local area network (LAN) communication module or a power line communication (PLC) module). A corresponding one of these communication modules may communicate with the external electronic device via the first network 398 (e.g., a short-range communication network, such as Bluetooth™, wireless-fidelity (Wi-Fi) direct, or infrared data association (IrDA)) or the second network 399 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 392 may identify and authenticate the electronic device 301 in a communication network, such as the first network 398 or the second network 399, using subscriber information (e.g., international mobile subscriber identity (IMSI)) stored in the subscriber identification module 396.

The antenna module 397 may transmit or receive a signal or power to or from the outside (e.g., the external electronic device) of the electronic device 301. According to an embodiment, the antenna module 397 may include one or more antennas, and, therefrom, at least one antenna appropriate for a communication scheme used in the communication network, such as the first network 398 or the second network 399, may be selected, for example, by the communication module 390 (e.g., the wireless communication module 392). The signal or the power may then be transmitted or received between the communication module 390 and the external electronic device via the selected at least one antenna.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 301 and the external electronic device 304 via the server 308 coupled with the second network 399. Each of the electronic devices 302 and 304 may be a device of a same type as, or a different type, from the electronic device 301. According to an embodiment, all or some of operations to be executed at the electronic device 301 may be executed at one or more of the external electronic devices 302, 304, or 308. For example, if the electronic device 301 should perform a function or a service automatically, or in response to a request from a user or another device, the electronic device 301, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 301. The electronic device 301 may provide the outcome, with or without further processing of the outcome, as at least part of a reply to the request. To that end, a cloud computing, distributed computing, or client-server computing technology may be used, for example.

Figure 4A:
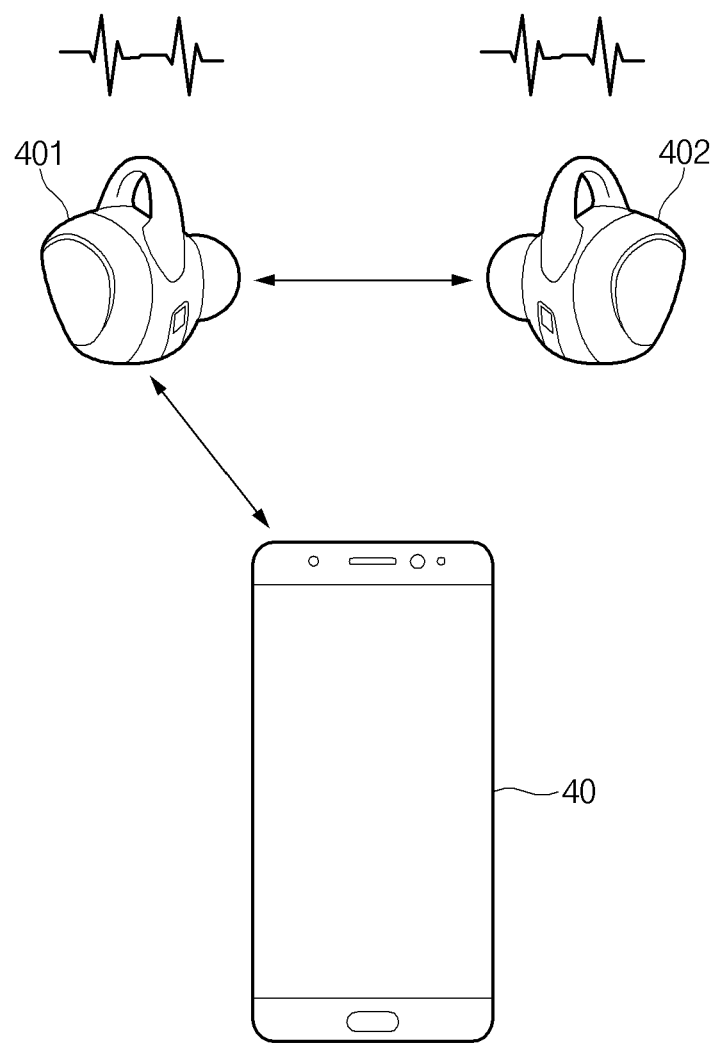
FIGS. 4A and 4B are views for describing how to determine whether an audio output device is worn by a plurality of users, according to an embodiment of the disclosure.
Figure 4B:
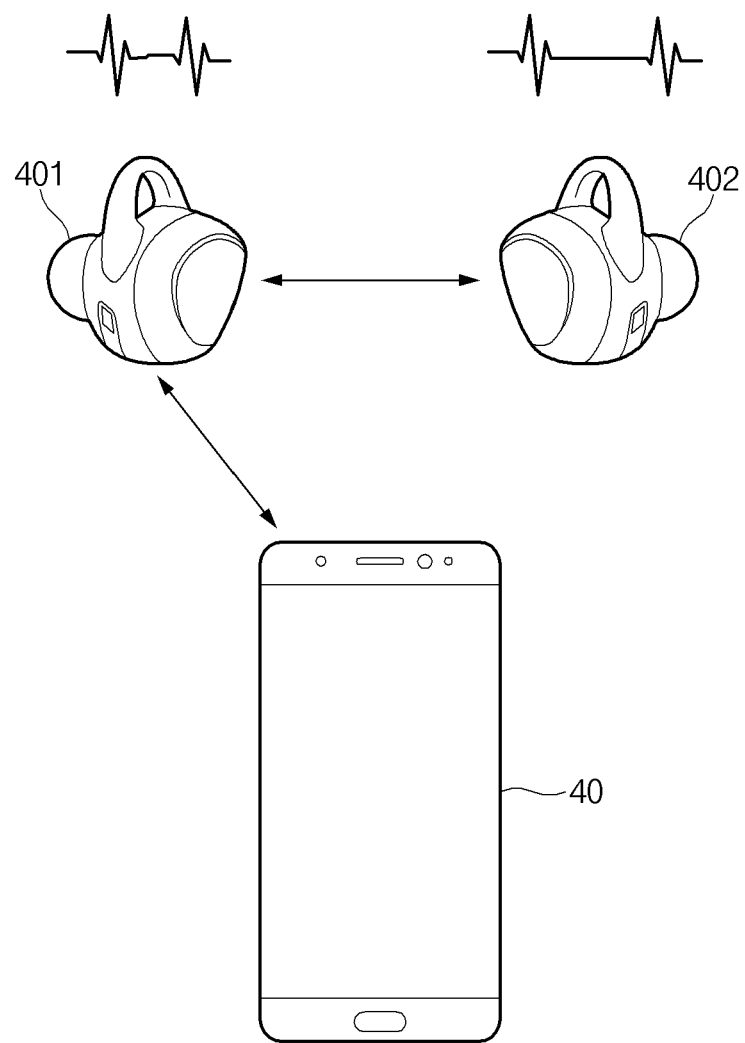

FIGS. 4A and 4B are views for describing how to determine whether an audio output device is worn by a plurality of users, according to an embodiment of the disclosure.

Referring to FIGS. 4A and 4B, an external electronic device 40 may communicate with a first output device 401 and a second output device 402. For example, the external electronic device 40, the first output device 401, and the second output device 402 may correspond to the external electronic device 10, the first output device 101, and the second output device 102 illustrated in FIG. 1. An example is illustrated in FIGS. 4A and 4B as the external electronic device 40 communicates with the first output device 401, but the external electronic device 40 may communicate with the second output device 402 or may communicate with the first output device 401 and the second output device 402.

According to an embodiment, the first output device 401 may receive information sensed by the second output device 402. For example, the first output device 401 may determine operation states of the first output device 401 and the second output device 402 based at least on information sensed by the first output device 401 and information sensed by the second output device 402.

According to an embodiment, the first output device 401 may determine an operation state based on biometric information (e.g., heartbeat information). Referring to FIG. 4A, the same heartbeat information (e.g., a heart rate, a heartbeat timing, a heartbeat interval, a heartbeat waveform, and/or a heartbeat frequency) is sensed by the first output device 401 and the second output device 402. In this case, the first output device 401 may determine that the first output device 401 and the second output device 402 are used by the same user. Referring to FIG. 4B, different heartbeat information is sensed by the first output device 401 and the second output device 402. In this case, the first output device 401 may determine that the first output device 401 and the second output device 402 are used by different users.

According to another embodiment, the first output device 401 may determine an operation state based on non-biometric information (e.g., an output direction and/or a distance). For example, referring to FIG. 4A, the first output device 401 and the second output device 402 may face the same point. In this case, the first output device 401 may determine that the first output device 401 and the second output device 402 are used by the same user. Referring to FIG. 4B, the first output device 401 and the second output device 402 may face different points. In this case, the first output device 401 may determine that the first output device 401 and the second output device 402 are used by different users. For example, the first output device 401 may determine directions in which the first output device 401 and the second output device 402 face, based on angular velocity and/or acceleration information of the first output device 401 and the second output device 402 obtained by using sensing modules (e.g., the sensing module 251 of FIG. 2 and the sensing module 252 of FIG. 2) of the first output device 401 and the second output device 402. For another example, returning to FIG. 4A, in the case where the first output device 401 is spaced from the second output device 402 by a specified distance or more, the first output device 401 may determine that the first output device 401 and the second output device 402 are used by different users. For example, the first output device 401 may determine a distance between the first output device 401 and the second output device 402, based at least on an intensity of a communication signal or a response speed through communication circuits (e.g., the communication circuit 261 of FIG. 2 and the communication circuit 262 of FIG. 2) of the first output device 401 and the second output device 402.

According to an embodiment, when it is determined that the first output device 401 and the second output device 402 are used by different users, the first output device 401 may transmit information corresponding to the use by the plurality of users to the external electronic device 40.

In the above embodiments, a description is given as whether the first output device 401 and the second output device 402 are used by the same user is determined by the first output device 401, but whether the first output device 401 and the second output device 402 are used by the same user may be determined by the external electronic device 40. For example, the external electronic device 40 may receive information sensed by the first output device 401 and the second output device 402 through the first output device 401. For another example, the external electronic device 40 may receive information sensed by the first output device 401 from the first output device 401 and may receive information sensed by the second output device 402 from the second output device 402.

The operation states of the first output device 401 and the second output device 402 may be determined as described above. Below, a method in which an electronic device displays an operation state based on determining the operation state will be described with reference to FIG. 5.

Figure 5:
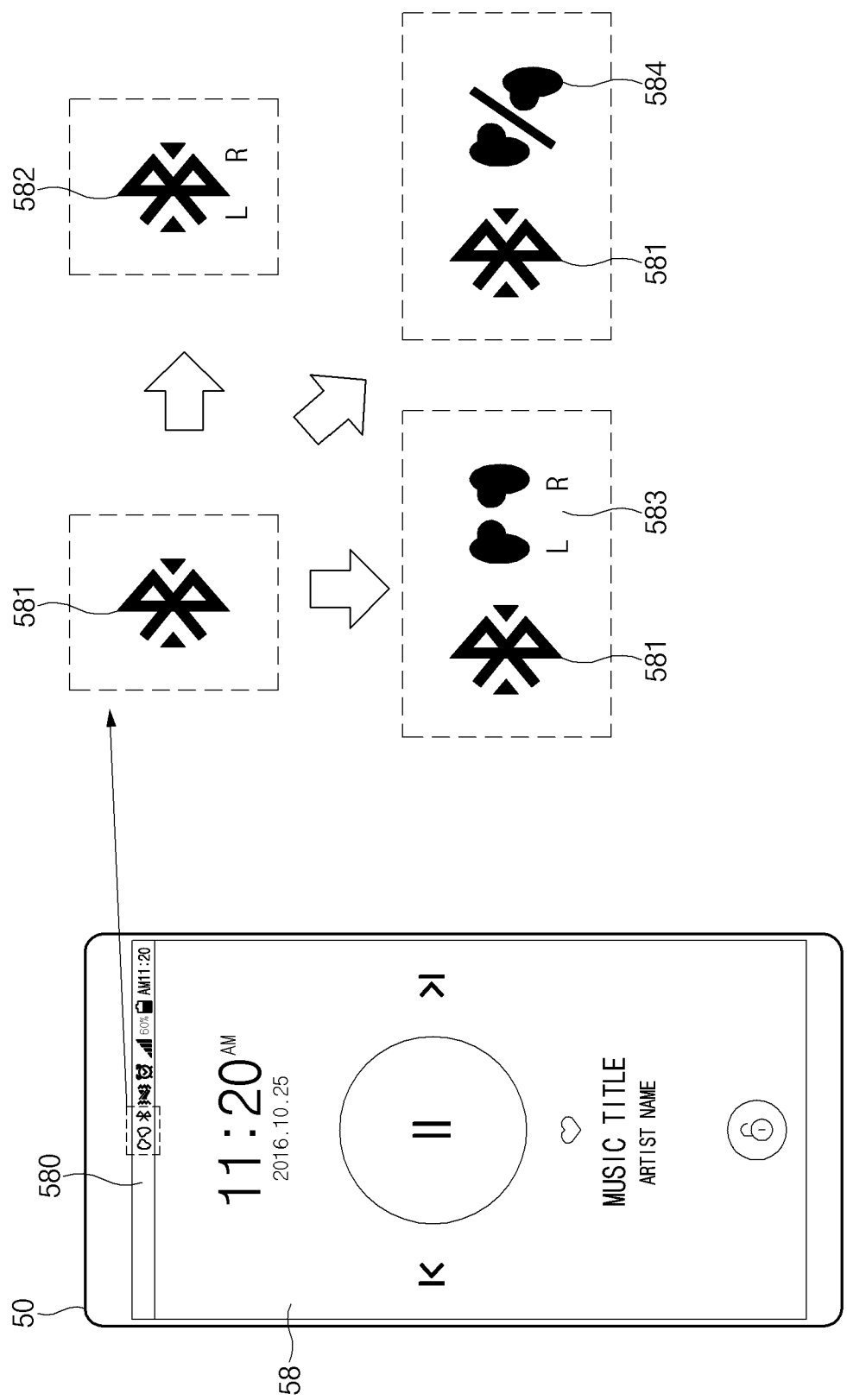
FIG. 5 is a view illustrating a method in which an electronic device displays an operation state of an audio output device, according to an embodiment of the disclosure.

FIG. 5 is a view illustrating a method in which an electronic device displays an operation state of an audio output device, according to an embodiment of the disclosure.

Referring to FIG. 5, according to an embodiment, an electronic device 50 (e.g., the external electronic device 10 of FIG. 1) may display operation state information indicating an operation state of an external audio output device (e.g., the audio output device 100 of FIG. 1) in at least a portion on a display 58 (e.g., the display device 360 of FIG. 3). For example, the electronic device 50 may display the operation state information in a first display area 580 on the display 58.

According to an embodiment, the electronic device 50 may display the operation state information by using at least one of an image, a character, an icon, or a pop-up message. For example, when the operation state information is changed, the electronic device 50 may display the changed operation state information on the display 58 by using a pop-up message. For example, the operation state information may be information indicating whether the external audio output device is used by a plurality of users.

According to an embodiment, the electronic device 50 may display an operation state of an external audio device on a first display area 580 (e.g., a task bar, an indicator, or a notification bar) by using at least one icon. For example, in the case where the external audio device is connected (e.g., paired) with the electronic device 50, the electronic device 50 may display a first icon 581 (e.g., a Bluetooth icon) indicating a connection of the external audio device in the first display area 580. Also, in the case where the external audio output device is used by a plurality of users, the electronic device 50 may display a change of the operation state of the external audio output device on the first display area 580. For example, the electronic device 50 may display a second icon 582 changed from the first icon 581 on the first display area 580. For another example, the electronic device 50 may display a third icon 583 or a fourth icon 584 indicating operation state information corresponding to a plurality of users on the first display area 580 together with the first icon 581.

Meanwhile, shapes of the icons illustrated in FIG. 5 are exemplary, and icon shapes are not limited thereto. Also, according to an embodiment, the electronic device 50 may notify a change of an operation state through a visual, auditory, and/or tactile notification.

The notification method according to a change of the operation state of the external audio output device is described with reference to FIG. 5. As described above, in the case where an external audio output device is used by different users (e.g., in the case where the external audio output device is used by a plurality of users), a first output device (e.g., the first output device 101 of FIG. 1) and a second output device (e.g., the second output device 102 of FIG. 1) of the external audio output device may operate independently of each other. Below, an independent control method of an external audio output device according to an operation state will be described with reference to FIGS. 6A and 6B.

Figure 6A:
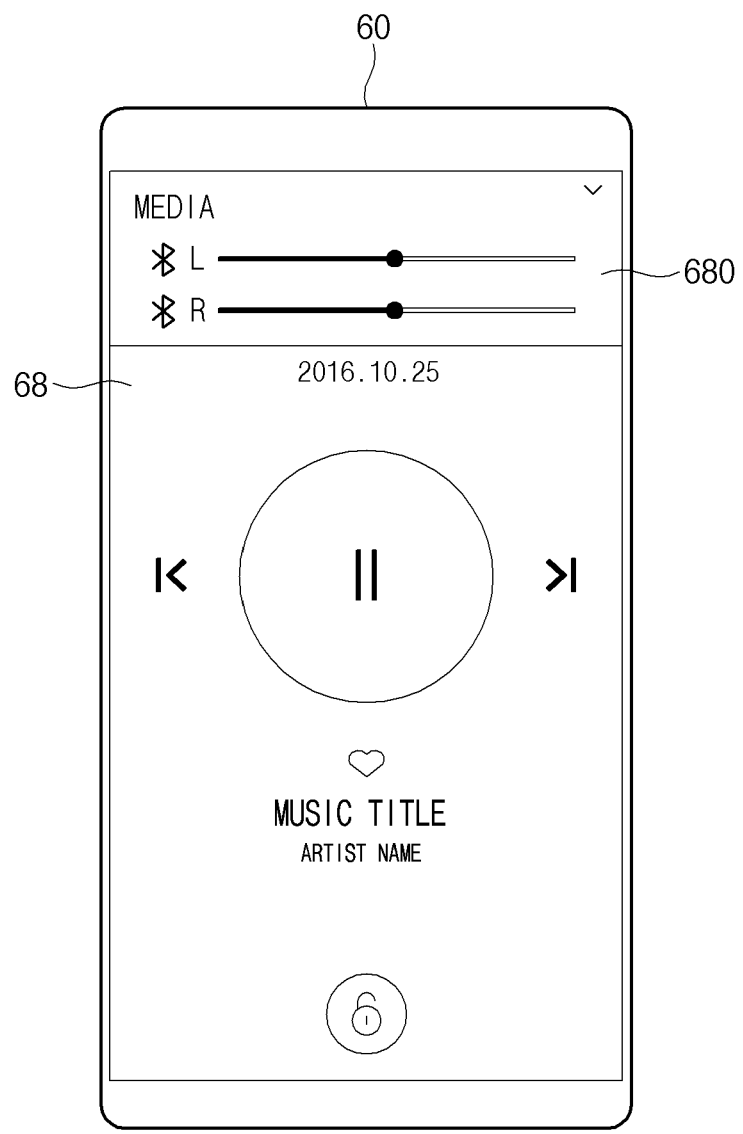
FIG. 6A illustrates a user interface for an independent volume control of an audio output device, according to an embodiment of the disclosure.

FIG. 6A illustrates a user interface for an independent volume control of an audio output device, according to an embodiment of the disclosure.

Referring to FIG. 6A, according to an embodiment, an electronic device 60 (e.g., the external electronic device 10 of FIG. 1) may display a user interface for controlling an operation of an external audio output device (e.g., the audio output device 100 of FIG. 1) in at least a portion on a display 68 (e.g., the display device 360 of FIG. 3). For example, in the case where the external audio output device is used by a plurality of users, the electronic device 60 may display a user interface 680 for controlling the external audio output device in a specified area (or a partial area) on the display 68. For example, in the case where the external audio output device is used by a plurality of users, the electronic device 60 may display the user interface 680 including a first user interface for controlling a first output device of the external audio output device and a second user interface for controlling a second output device of the external audio output device in a specified area (or a partial area) on the display 68.

According to an embodiment, a user interface may be an interface for adjusting an output volume of the external audio output device. For example, when a user input for adjusting an output volume is received, the electronic device 60 may display the user interface 680 on the display 68. For example, the user input for adjusting the output volume of the external audio output device may be received through the electronic device 60 or the external audio output device.

According to an embodiment, the electronic device 60 may display the user interface 680 at a specified location of the display 68. For example, the electronic device 60 may display the user interface 680 on the top, the center, or the bottom of the display 68. For another example, the electronic device 60 may display the user interface 680 at a location on the display 68, which is adjacent to a physical button for a volume control of the electronic device 60.

Figure 6B:
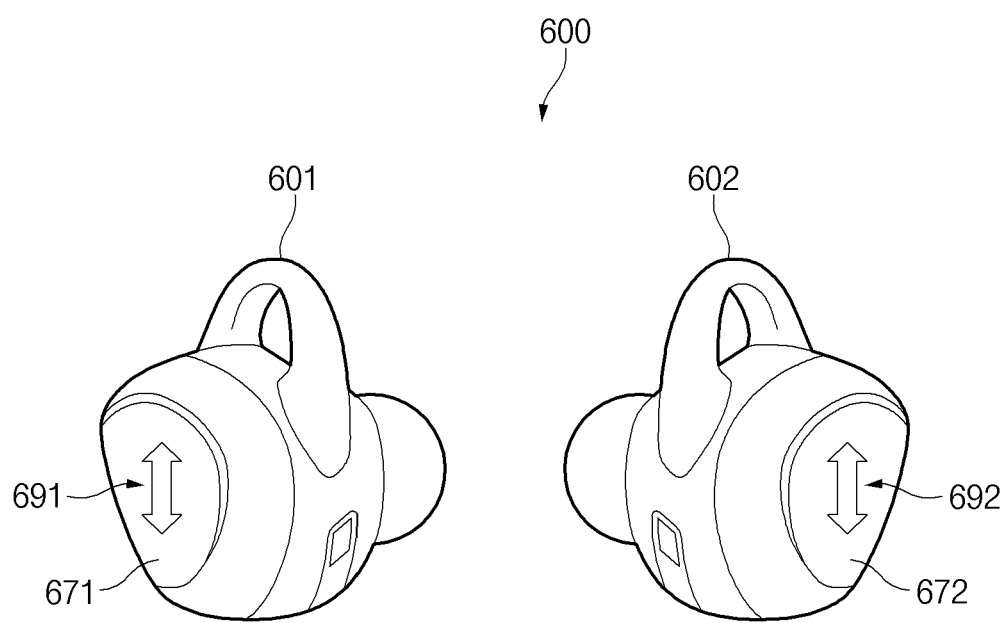
FIG. 6B illustrates an independent volume control of an audio output device, according to an embodiment of the disclosure.

FIG. 6B illustrates an independent volume control of an audio output device, according to an embodiment of the disclosure.

According to an embodiment, referring to FIG. 6B, a first output device 601 (e.g., the first output device 101 of FIG. 1) and a second output device 602 (e.g., the second output device 102 of FIG. 1) of an external audio output device 600 (e.g., the audio output device 100 of FIG. 1) may include a first touch sensor 671 and a second touch sensor 672, respectively. For example, a first user input 691 may correspond to an input for a volume control received by the first output device 601, and a second user input 692 may correspond to an input a volume control received by the second output device 602. However, the first touch sensor 671 and the second touch sensor 672 are exemplary input devices, and input devices of the first output device 601 and the second output device 602 are not limited thereto. For another example, the first output device 601 may include a first input device, and the second output device 602 may include a second input device. For example, the first input device and the second input device may include at least one button (e.g., a button which may receive a push input, a roll input, a scroll input, and/or a toggle input). According to an embodiment, an independent volume control may be performed based on whether the first output device 601 and the second output device 602 are used by the same user. For example, depending on whether the first output device 601 and the second output device 602 are used by the same user, different operations may be performed in response to the first user input 691 and the second user input 692.

According to an embodiment, the first output device 601 and the second output device 602 may be used by the same user. For example, each of the first output device 601 and the second output device 602 may adjust a volume of the external audio output device 600. For example, referring to FIG. 6A, the electronic device 60 may display only one scroll bar for a volume control in a specified area (or a partial area) on the display 68. For another example, the first output device 601 may adjust a volume of the external audio output device 600 in response to the first user input 691 and may change a sound source to be played in response to the second user input 692.

According to an embodiment, returning to FIG. 6B, the first output device 601 and the second output device 602 may be used by different users. For example, the first output device 601 may adjust a volume of the first output device 601 in response to the first user input 691. For another example, the second output device 602 may adjust a volume of the second output device 602 in response to the second user input 692. For example, referring to FIG. 6A, when the first user input 691 or the second user input 692 is received, the electronic device 60 may display two scroll bars for respectively adjusting volumes of the first output device 601 and the second output device 602 on the user interface 680.

Embodiments associated with a volume control are described with reference to FIGS. 6A and 6B. However, an independent control of the first output device 601 and the second output device 602 is not limited thereto. For example, an output mode (e.g., a stereo mode or a mono mode), an output characteristic, and/or an independent sound source control of the first output device 601 and the second output device 602 may be applied to the first output device 601 and the second output device 602. Below, various embodiments associated with an independent control will be described with reference to FIGS. 7, 8, 9A, and 9B.

Figure 7:
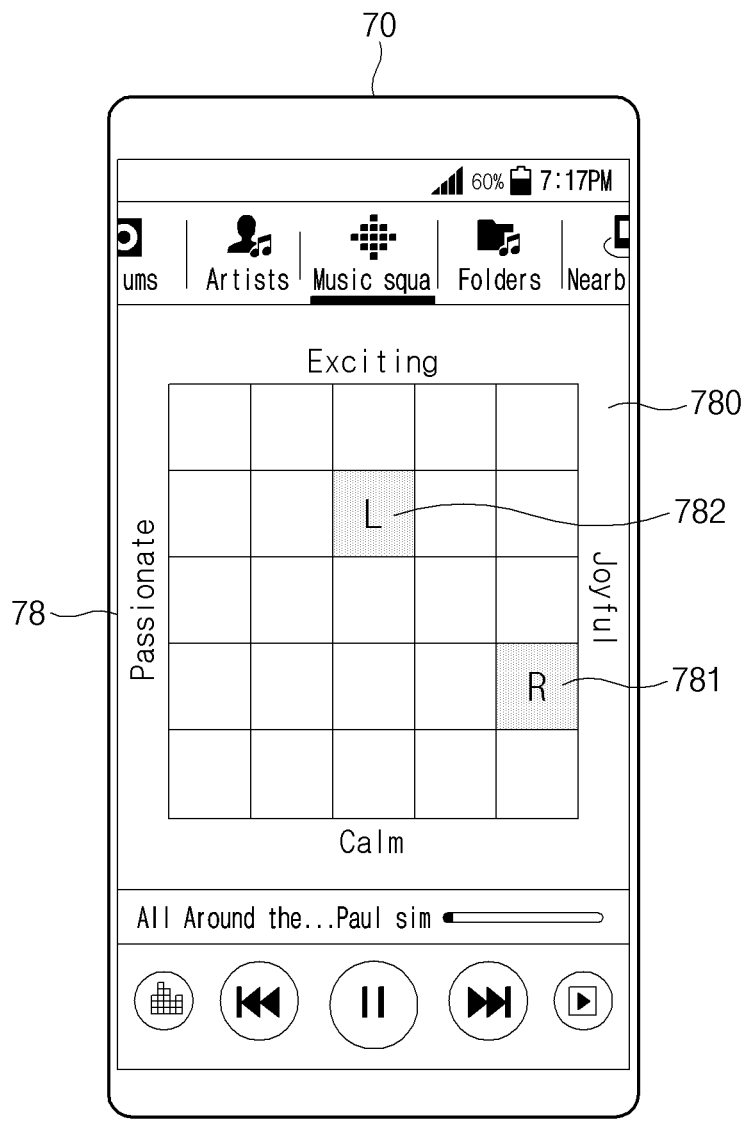
FIG. 7 illustrates a user interface for independent music recommendation of an audio output device, according to an embodiment of the disclosure.

FIG. 7 illustrates a user interface for independent music recommendation of an audio output device, according to an embodiment of the disclosure.

Referring to FIG. 7, according to an embodiment, an electronic device 70 (e.g., the electronic device 10 of FIG. 1) may display a music recommendation user interface (e.g., a music square) in a first display area 780 on a display 78 (e.g., the display device 360 of FIG. 3). For example, the music recommendation user interface may include at least one area for setting a plurality of references (e.g., emotion, genre, tempo, or mood). For example, the music recommendation user interface may include a grid for setting the plurality of references. For example, the electronic device 70 may display the music recommendation user interface in response to an input to at least a partial area on the display 78. According to another embodiment, in the case where a first output device (e.g., the first output device 101 of FIG. 1) and a second output device (e.g., the second output device 102 of FIG. 1) of an external audio output device (e.g., the audio output device 100 of FIG. 1) are used by different users, the electronic device 70 may display an user interface for independent music recommendation of the first output device and the second output device on the first display area 780. For example, in response to an input to a first icon 781, the electronic device 70 may recommend music corresponding to a location of the first icon 781 to a user for the output of the first output device. For another example, in response to an input to a second icon 782, the electronic device 70 may recommend music corresponding to a location of the second icon 782 to the user for the output of the second output device.

According to an embodiment, the electronic device 70 may display a music selection user interface in the first display area 780 on the display 78. For example, the music selection user interface may include at least one area for setting a plurality of references (e.g., emotion, genre, tempo, or mood). For example, the music selection user interface may include a grid for setting the plurality of references. For example, the electronic device 70 may display the music selection user interface in response to an input to at least a partial area on the display 78. According to another embodiment, in the case where a first output device (e.g., the first output device 101 of FIG. 1) and a second output device (e.g., the second output device 102 of FIG. 1) of an external audio output device (e.g., the audio output device 100 of FIG. 1) are used by different users, the electronic device 70 may display an user interface for independent music selection of the first output device and the second output device on the first display area 780. For example, in response to an input to the first icon 781, the electronic device 70 may output at least one sound source corresponding to a location of the first icon 781 through the first output device. For another example, in response to an input to the second icon 782, the electronic device 70 may output at least one sound source corresponding to a location of the second icon 782 through the second output device.

According to an embodiment, the first icon 781 and the second icon 782 may be different from each other in at least one of a color, a size, or a shape.

Figure 8:
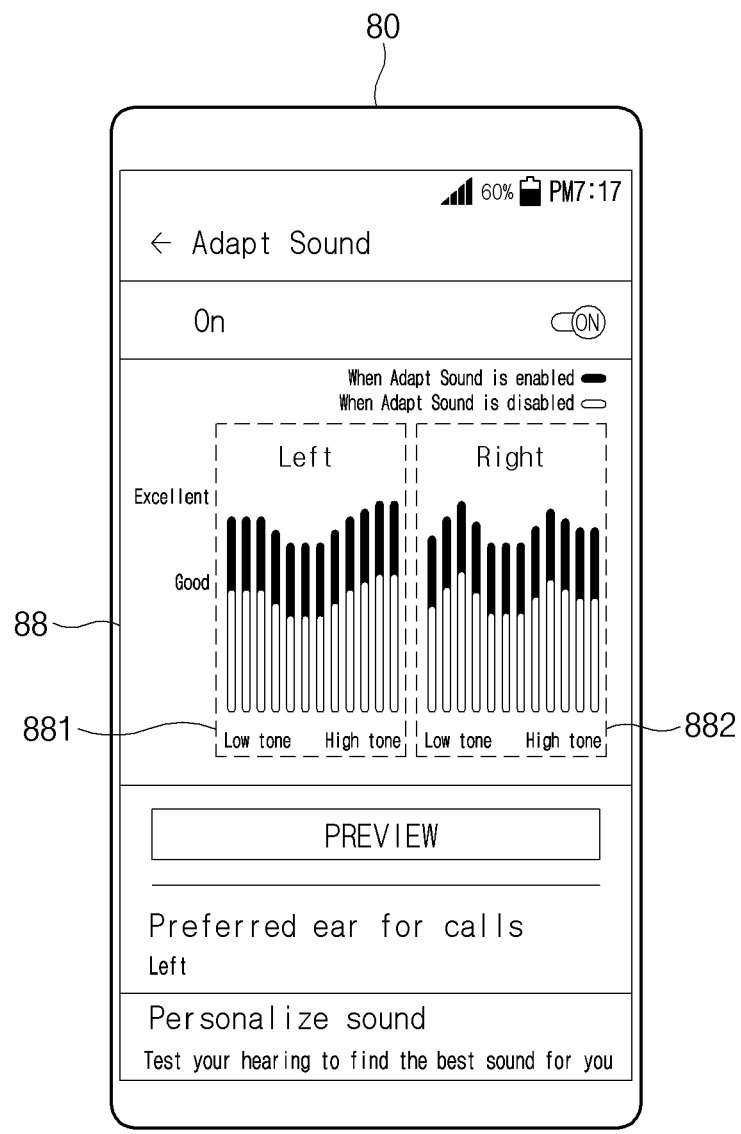
FIG. 8 illustrates a user interface for an independent audio output characteristic control of an audio output device, according to an embodiment of the disclosure.

FIG. 8 illustrates a user interface for an independent audio output characteristic control of an audio output device, according to an embodiment of the disclosure.

Referring to FIG. 8, according to an embodiment, an electronic device 80 (e.g., the external electronic device 10 of FIG. 1) may display a user interface (e.g., an equalizer) for controlling an output characteristic of an external audio output device (e.g., the audio output device 100 of FIG. 1) in at least a portion on a display 88 (e.g., the display device 360 of FIG. 3). For example, the output characteristic control user interface may include a user interface for setting a volume for each of a plurality of frequency bands.

According to an embodiment, in the case where a first output device (e.g., the first output device 101 of FIG. 1) and a second output device (e.g., the second output device 102 of FIG. 1) of an external audio output device (e.g., the audio output device 100 of FIG. 1) are used by different users, the electronic device 80 may display an user interface for an independent output characteristic control of the first output device and the second output device on at least a portion of the first display area. For example, the electronic device 80 may display a first user interface 881 indicating an output characteristic of the first output device and a second user interface 882 indicating an output characteristic of the second output device in at least a portion of the display 88.

According to an embodiment, in the case where the first output device and the second output device are used by different users, the electronic device 80 or the first output device may apply a hearing correction system (e.g., Samsung's adaptive sound) to the first output device and the second output device. For example, the electronic device 80 or the first output device may apply the hearing correction system by using hearing data of a user stored in the electronic device 80 or the first output device. For another example, in the case where the second output device is used by a different user, the electronic device 80 or the first output device may apply the hearing correction system to the second output device by using hearing data of the different user, which are associated with the second output device and are provided from an external electronic device adjacent to the second output device.

Figure 9A:
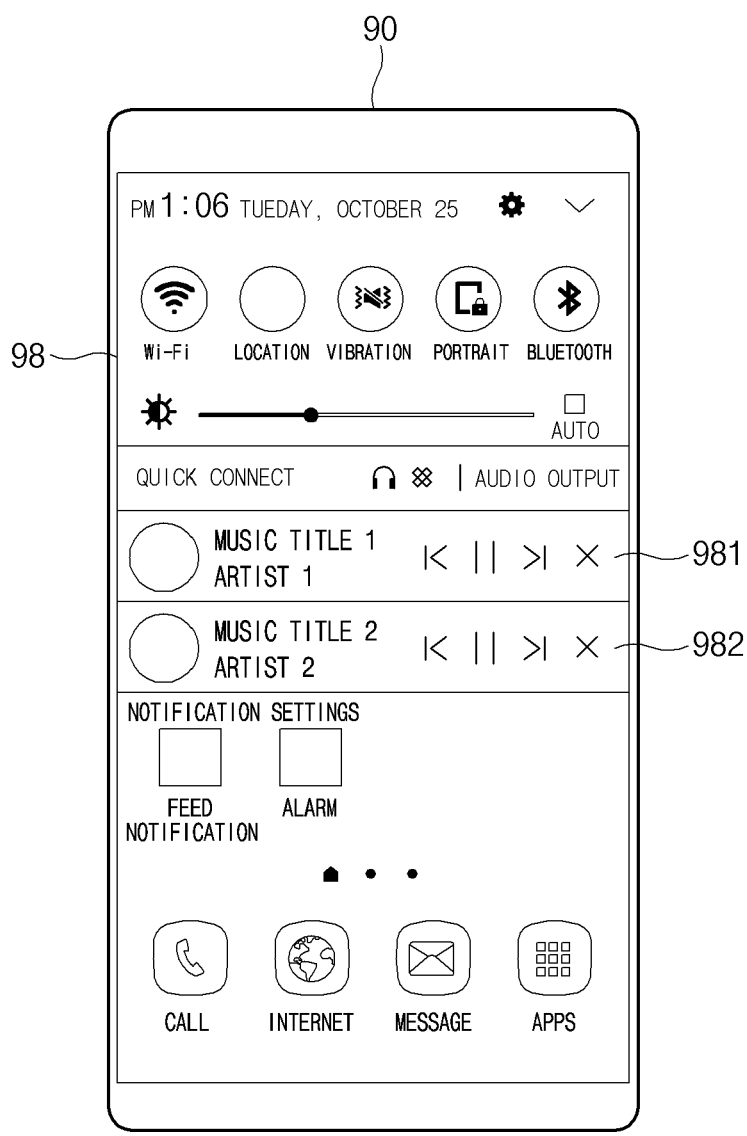
FIGS. 9A and 9B illustrate user interfaces for an independent volume control of an audio output device, according to various embodiments of the disclosure.
Figure 9B:
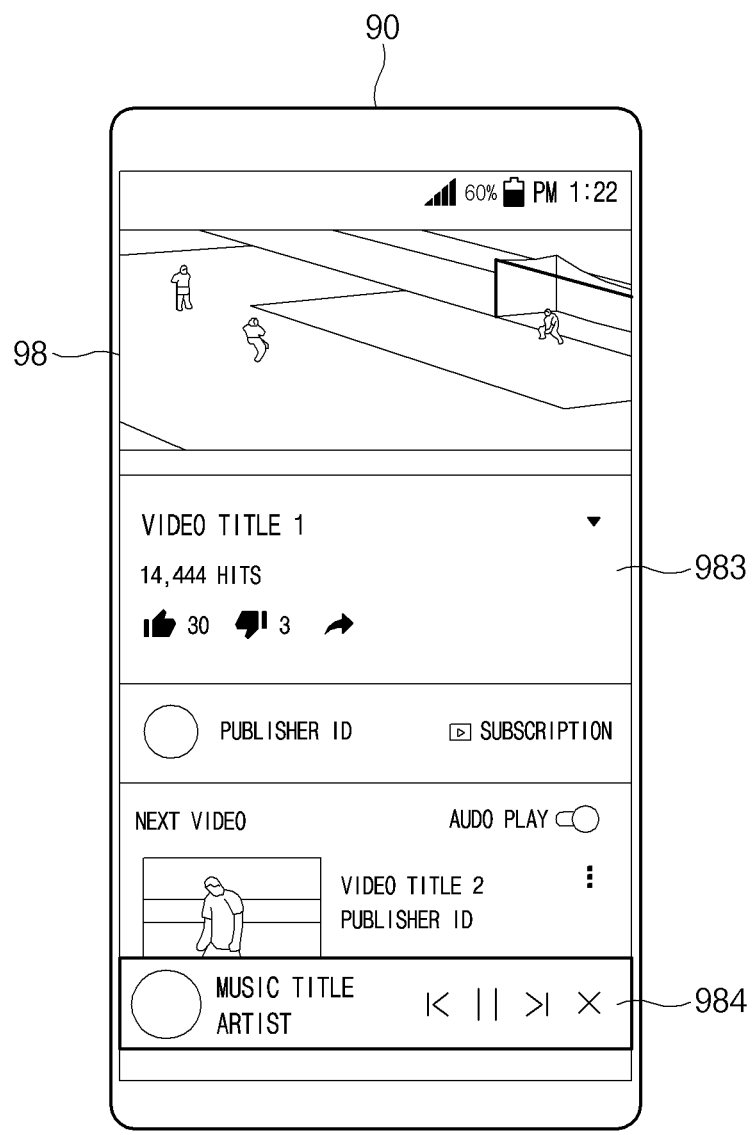

FIGS. 9A and 9B illustrate user interfaces for an independent volume control of an audio output device, according to various embodiments of the disclosure.

Referring to FIG. 9A, according to an embodiment, in the case where an external audio output device (e.g., the audio output device 100 of FIG. 1) is used by a plurality of users, an electronic device 90 may assign different tasks to a first output device (e.g., the first output device 101 of FIG. 1) and a second output device (e.g., the second output device 102 of FIG. 1) of the external audio output device.

According to an embodiment, the electronic device 90 may allow the first output device and the second output device to play different sound sources. For example, the electronic device 90 may allow the first output device and the second output device to play different sound sources based on a user input.

According to an embodiment, the electronic device 90 may display information about a sound source associated with the first output device in a first area 981 of a display 98 (e.g., the display device 360 of FIG. 3), and may display information about a sound source associated with the second output device in a second area 982.

Referring to FIG. 9B, according to an embodiment, the electronic device 90 may allow the first output device and the second output device to play sound sources corresponding to different applications. For example, the electronic device 90 may allow the first output device to play a sound source associated with a video player application and may allow the second output device to play a sound source associated with a music player application. For example, when an additional input is received while playing a video, the electronic device 90 may allow the second output device to play a sound source associated with the music player application.

According to an embodiment, the electronic device 90 may display information about an application associated with the first output device in a third area 983 of the display 98, and may display information about an application associated with the second output device in a fourth area 984.

A description is given with reference to FIGS. 9A and 9B as the independent control of the external audio output device is performed by the electronic device 90, but at least a portion of the operation of the electronic device 90 may be performed by the first output device of the external audio output device.

According to an embodiment, the electronic device 90 may control the first output device and the second output device by using a communication with the first output device and the second output device. According to another embodiment, the electronic device 90 may control the first output device and the second output device by using a communication with the first output device or the second output device. For example, the electronic device 90 may control the first output device and the second output device by communicating with a master device of the external audio output device. Below, a master device selecting method will be described with reference to FIG. 10.

Figure 10:
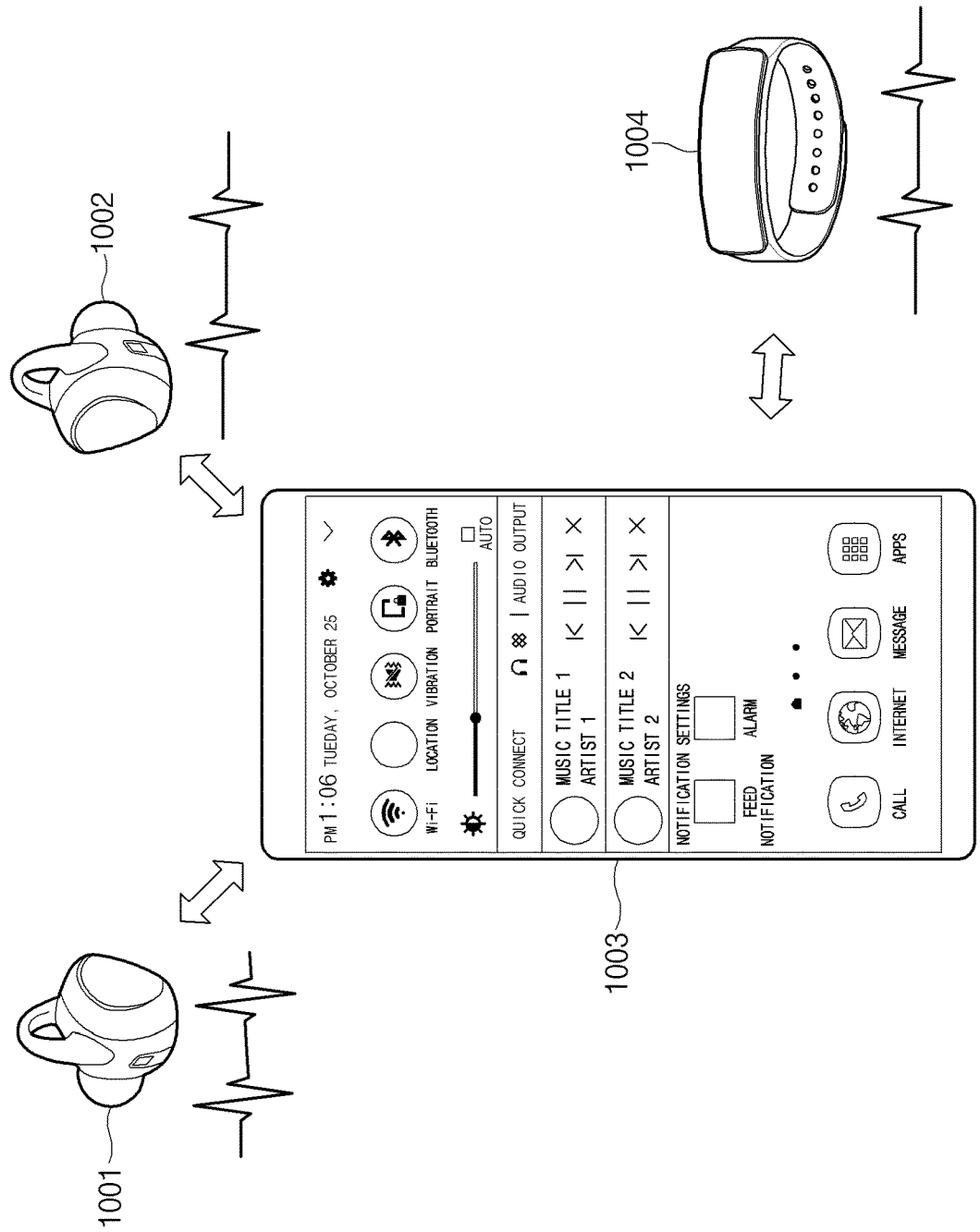
FIG. 10 illustrates a master device setting method, according to an embodiment of the disclosure.

FIG. 10 illustrates a master device setting method, according to an embodiment of the disclosure.

Referring to FIG. 10, according to an embodiment, an electronic device 1003 (e.g., the external electronic device 10 of FIG. 1) may determine a master device based on heartbeat information of an external electronic device 1004. For example, the external electronic device 1004 may be a wearable device (e.g., a smart watch) which may be mounted on user's body and may include an HR sensor. For example, the external electronic device 1004 may be a device which communicates with the electronic device 1003.

According to an embodiment, the electronic device 1003 may receive first heartbeat information, second heartbeat information, and third heartbeat information from a first output device 1001 (e.g., the first output device 101 of FIG. 1), a second output device 1002 (e.g., the second output device 102 of FIG. 1), and the external electronic device 1004, respectively.

According to an embodiment, the electronic device 1003 may determine a master device of the first output device 1001 and the second output device 1002 based at least on the first heartbeat information, the second heartbeat information, and the third heartbeat information. For example, the electronic device 1003 may determine a device, which has the highest similarity with the third heartbeat information or corresponds to heartbeat information having a similarity of a specified magnitude or more, from among the first output device 1001 and the second output device 1002 as a master device. For example, it may be determined that the second heartbeat information of the second output device 1002 and the third heartbeat information of the external electronic device 1004 are identical. In this case, the electronic device 1003 may set the second output device 1002 to a master device. Also, the electronic device 1003 may set the first output device 1001 to a slave device.

According to an embodiment, one output device of the first output device 1001 and the second output device 1002 may be in advance set to a master device. For example, the first output device 1001 may be set to a default master device. According to another embodiment, the electronic device 1003 may set one output device of the first output device 1001 and the second output device 1002 to a master device based on a user input. For example, the electronic device 1003 may set one output device of the first output device 1001 and the second output device 1002 to a master device based on a user input to the electronic device 1003, a user input to the first output device 1001, and/or a user input to the second output device 1002.

According to an embodiment, the first output device 1001, the second output device 1002, and the external electronic device 1004 may measure biometric information (e.g., a heartbeat, a fatigue level, a galvanic skin reflex (GSR), a body temperature, and/or a blood sugar) by using an optical and/or electrical method. For example, the first output device 1001, the second output device 1002, and the external electronic device 1004 may obtain biometric information by applying a light having a wavelength in a specified range to a skin of a wearer. For example, the first output device 1001, the second output device 1002, and the external electronic device 1004 may measure biometric information based at least on a current flowing through the skin of the wearer and/or a voltage measured on the skin of the wearer. The electronic device 1003 may set one output device of the first output device 1001 and the second output device 1002 to a master device based on a similarity of the biometric information obtained by the first output device 1001, the second output device 1002, and the external electronic device 1004. For example, the electronic device 1003 may determine a device, which has the highest similarity with the biometric information obtained by the external electronic device 1004 or corresponds to biometric information having a similarity of a specified magnitude or more, from among the first output device 1001 and the second output device 1002 as a master device.

According to an embodiment, the electronic device 1003 may set a master device based at least on a location of the first output device 1001, the second output device 1002, and/or the external electronic device 1004. For example, the electronic device 1003 may set an output device, which is close in distance to the electronic device 1003 and/or the external electronic device 1004, from among the first output device 1001 and the second output device 1002 to a master device. For another example, the electronic device 1003 may set an output device, which is out of a specified range from the electronic device 1003 and/or the external electronic device 1004, from among the first output device 1001 and the second output device 1002 to a slave device and may set the other output device to a master device. According to an embodiment, the electronic device 1003 may control the first output device 1001 and the second output device 1002 through the master device.

According to an embodiment, in the case where a notification such as an incoming call or a received message is, the electronic device 1003 may provide the notification only to a master device.

According to an embodiment, in the case where a state of a slave device is changed, the electronic device 1003 may notify the master device that the state of the slave device is changed. For example, the state change of the slave device may include at least one of a change of a user associated with the slave device, a change of a wearing state of the slave device, a change of a connection state of the slave device, or a change of a power state of the slave device.

A description is given with reference to FIG. 10 as one output device of the first output device 1001 and the second output device 1002 is set to a master device, but the setting of the master device is not limited thereto. For example, each of the first output device 1001 and the second output device 1002 may be set to a master device.

Figure 11:
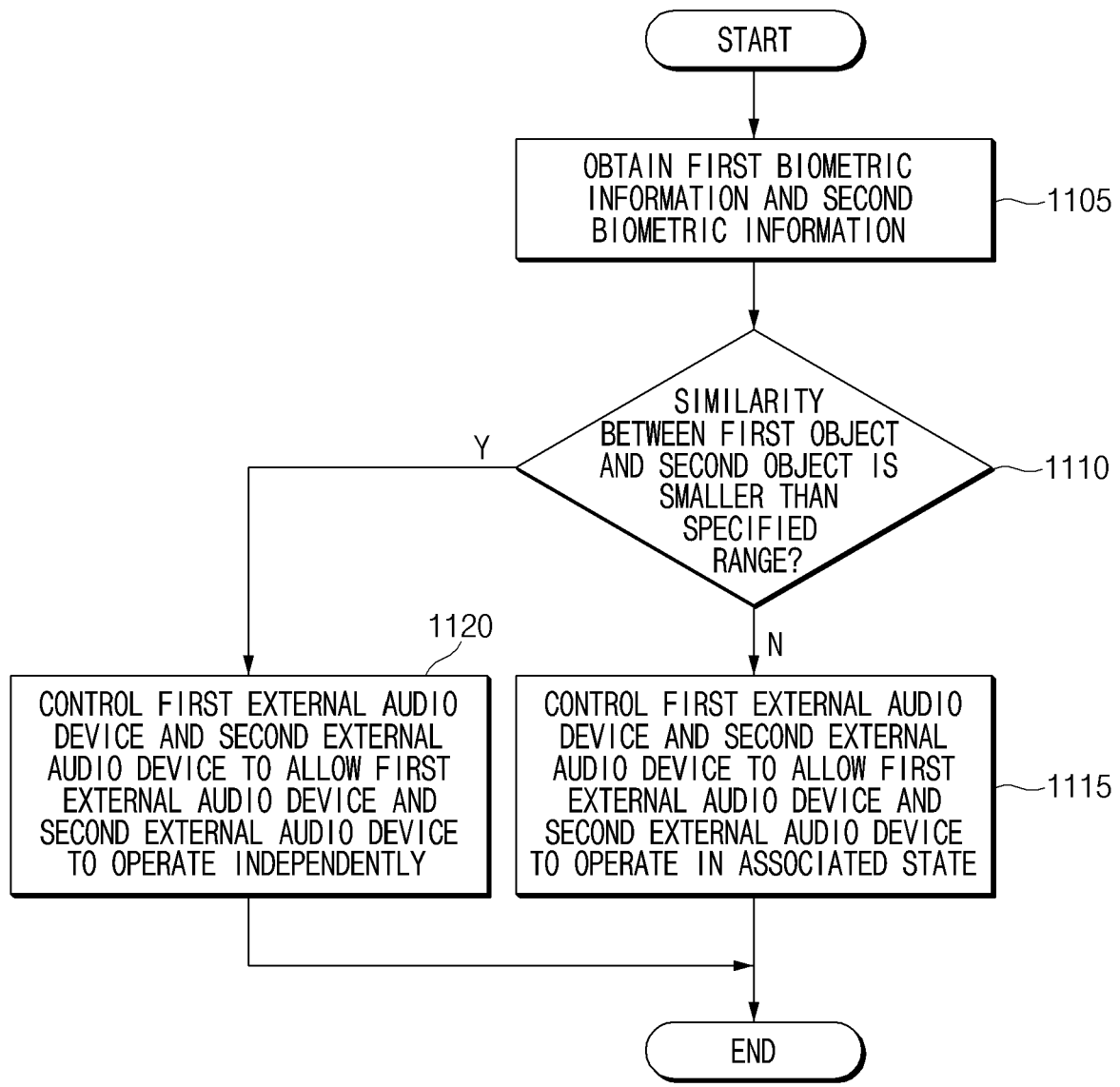
FIG. 11 is a flowchart illustrating a method in which an electronic device controls an external audio output device, according to various embodiments of the disclosure.

FIG. 11 is a flowchart illustrating a method in which an electronic device controls an external audio output device, according to various embodiments of the disclosure.

Referring to FIG. 11, in operation 1105, an electronic device (e.g., the external electronic device 10 of FIG. 1) may obtain first biometric information sensed by a first external audio device (e.g., the first output device 101 of FIG. 1) and second biometric information sensed by a second external audio device (e.g., the second output device 102 of FIG. 1). For example, the electronic device may obtain the first biometric information and the second biometric information from the first external audio device. For another example, the electronic device may obtain the first biometric information from the first external audio device and may obtain the second biometric information from the second external audio device. For example, the first biometric information may be sensed from a first object associated with the first external audio device. Also, for example, the second biometric information may be sensed from a second object associated with the second external audio device. For another example, biometric information may include heartbeat information.

In operation 1110, the electronic device may determine whether a similarity between the first object and the second object is not smaller than a specified range, based at least on the first biometric information and the second biometric information. For example, the electronic device may determine the similarity between the first object and the second object, based on a similarity between the first biometric information and the second biometric information. According to an embodiment, when the similarity is not smaller than the specified range, the electronic device may determine whether the similarity satisfies a first specified condition. When the similarity is smaller than the specified range, the electronic device may determine whether the similarity satisfies a second specified condition.

In the case where it is determined that the similarity satisfies the first specified condition, in operation 1115, the electronic device may control the first external audio device and the second external audio device such that the first external audio device and the second external audio device operate in an associated state. For example, the electronic device may control the first external audio device and the second external audio device to the associated state by setting the first external audio device. For another example, the electronic device may control the first external audio device and the second external audio device to the associated state by setting the first external audio device and the second external audio device. For another example, the electronic device may control the first external audio device and the second external audio device to a state in which the first external audio device is set to operate as a master device and the second external audio device is set to operate as a slave device.

In the case where it is determined that the similarity satisfies the second specified condition, in operation 1120, the electronic device may control the first external audio device and the second external audio device such that the first external audio device and the second external audio device operate independently of each other. For example, the electronic device may control the first external audio device and the second external audio device independently by setting the first external audio device. For another example, the electronic device may control the first external audio device and the second external audio device independently by setting the first external audio device and the second external audio device. For another example, the electronic device may control the first external audio device and the second external audio device to a state in which the first external audio device is set to operate and the second external audio device is set to operate as a master device.

For example, the electronic device may display an icon corresponding to an independent control of the first external audio device and the second external audio device on a display of the electronic device. For another example, in the case where the first external audio device and the second external audio device are controlled independently of each other, the electronic device may display a user interface for controlling the first external audio device and the second external audio device independently on the display in response to a user input. For example, the electronic device may provide a user interface for controlling output characteristics (e.g., a volume, a volume for each band, or a sound field effect) of the first external audio device and the second external audio device on the display. For another example, the electronic device may assign different sound sources and/or applications to the first external audio device and the second external audio device.

Figure 12:
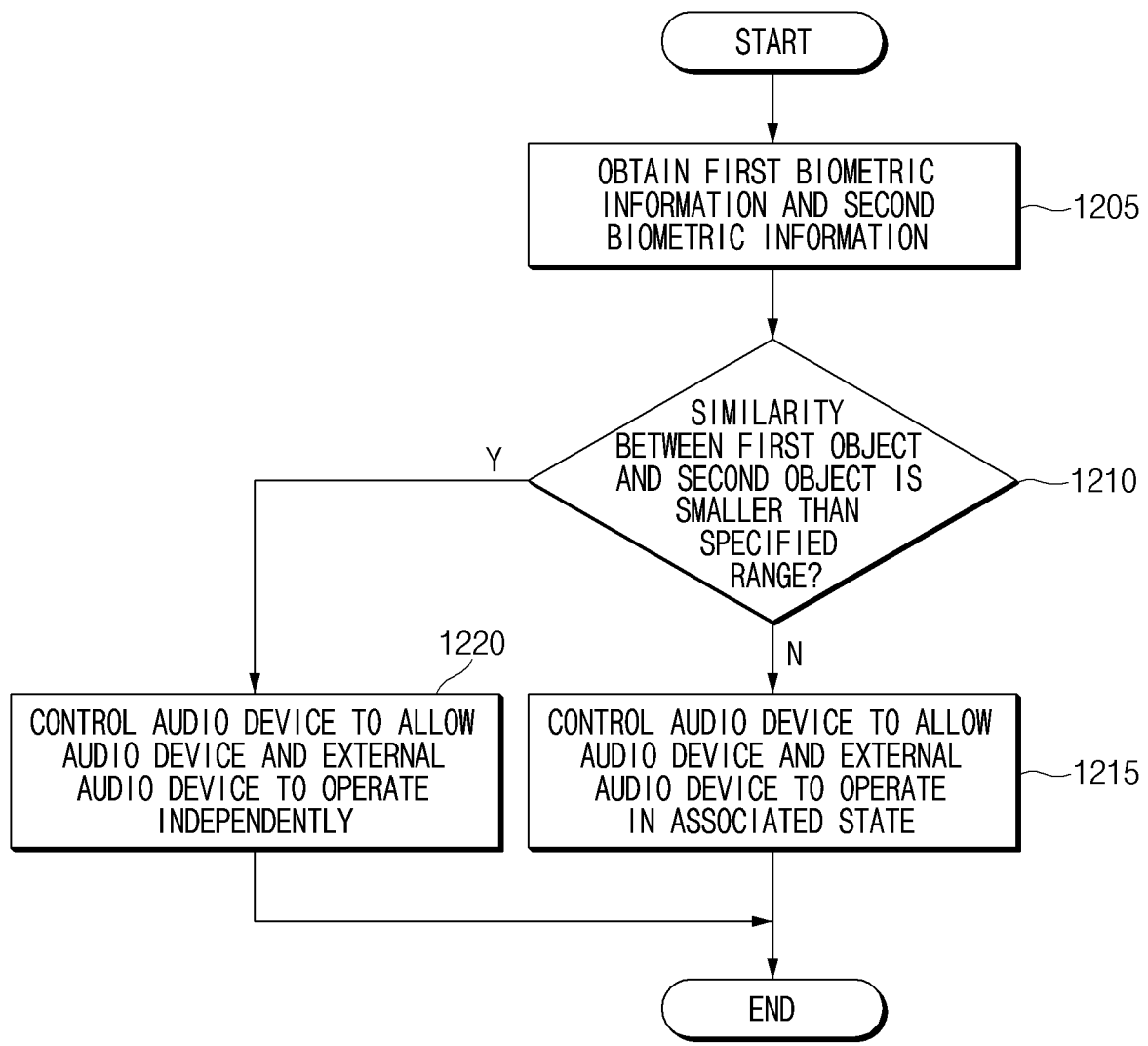
FIG. 12 is a flowchart illustrating an audio device control method, according to various embodiments of the disclosure.

FIG. 12 is a flowchart illustrating an audio device control method, according to various embodiments of the disclosure.

Referring to FIG. 12, in operation 1205, an audio device (e.g., the first output device 101 of FIG. 1) may obtain first biometric information and second biometric information. For example, the audio device may obtain the first biometric information of a first object associated with the audio device by using a sensor of the audio device. Also, for example, the audio device may obtain the second biometric information sensed by an external audio device (e.g., the second output device 102 of FIG. 1). For example, the second biometric information may be sensed from a second object associated with the external audio device. For another example, biometric information may include heartbeat information.

In operation 1210, the audio device may determine whether a similarity between the first object and the second object is not smaller than a specified range, based at least on the first biometric information and the second biometric information. For example, the audio device may determine the similarity between the first object and the second object, based on a similarity between the first biometric information and the second biometric information. According to an embodiment, when the similarity is not smaller than the specified range, the audio device may determine whether the similarity satisfies a first specified condition. When the similarity is smaller than the specified range, the audio device may determine whether the similarity satisfies a second specified condition.

In the case where it is determined that the similarity satisfies the first specified condition, in operation 1215, the audio device may set the audio device to allow the audio device and the external audio device to operate in an associated state. For example, the audio device may set the audio device so as to operate as a master device and may set the external audio device so as to operate as a slave device.

In the case where it is determined that the similarity satisfies the second specified condition, in operation 1220, the audio device may set the audio device to allow the audio device and the external audio device to operate independently of each other. For example, the audio device may set the audio device and the external audio device so as to operate as a master device.

For another example, when the first object and the second object are determined as being different, the audio device may transmit information corresponding to the use by a plurality of users to an external electronic device (e.g., the external electronic device 10 of FIG. 1).

For example, in the case where the audio device and the external audio device are controlled independently, the audio device may assign at least one of different sound sources, applications, sound field effects, volumes, or output characteristics to the audio device and the external audio device in response to a user input.

Figure 13:
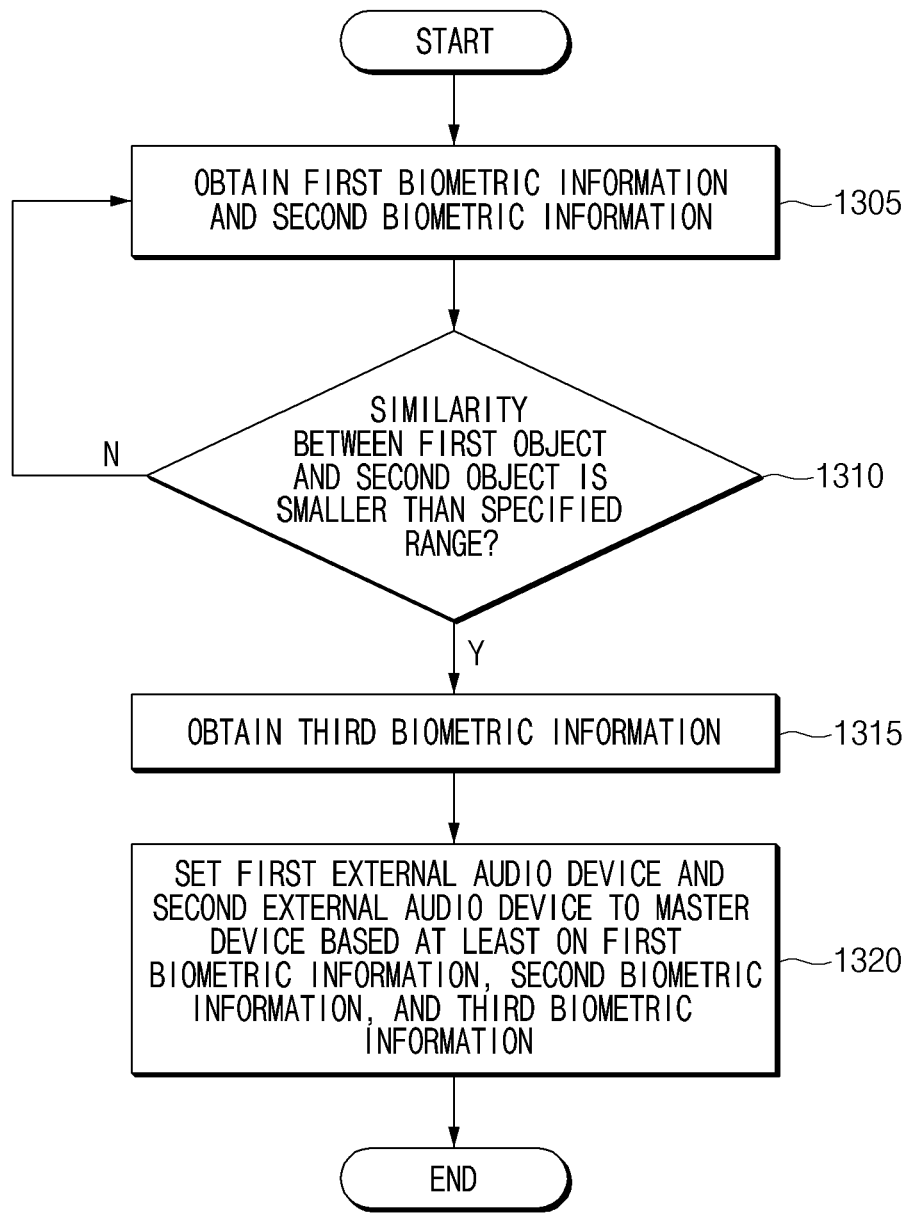
FIG. 13 is a flowchart illustrating a method in which an electronic device sets a master device, according to various embodiments of the disclosure.

FIG. 13 is a flowchart illustrating a method in which an electronic device sets a master device, according to various embodiments of the disclosure.

Referring to FIG. 13, in operation 1305, an electronic device (e.g., the external electronic device 10 of FIG. 1) may obtain first biometric information sensed by a first external audio device (e.g., the first output device 101 of FIG. 1) and second biometric information sensed by a second external audio device (e.g., the second output device 102 of FIG. 1). A detailed description associated with operation 1305 may be referenced by the description associated with operation 1105.

In operation 1310, the electronic device may determine whether a similarity between a first object and a second object is not smaller than a specified range, based at least on the first biometric information and the second biometric information. A detailed description associated with operation 1310 may be referenced by the description associated with operation 1110. In the case where it is determined in operation 1310 that the similarity is not smaller than the specified range, the electronic device may monitor whether the first object and the second object are identical. For example, the electronic device may perform operation 1305 periodically or randomly.

In the case where it is determined that the similarity is smaller than the specified range, in operation 1315, the electronic device may obtain third biometric information from an external electronic device (e.g., the external electronic device 1004 of FIG. 10) communicating with the electronic device.

In operation 1320, the electronic device may set one device selected from the first external audio device or the second external audio device, based at least on the first biometric information, the second biometric information, and the third biometric information. For example, the electronic device may determine a device, which has the highest similarity with the third biometric information or corresponds to biometric information having a similarity of a specified magnitude or more, as a master device.

According to an embodiment, the electronic device may control the first and second external audio devices through the master device. For example, in the case where a notification such as an incoming call or a received message is present, the electronic device may provide the notification only to the master device. For another example, in the case where a state of a slave device is changed, the electronic device may notify the master device that the state of the slave device is changed. For example, a state change of the slave device may include at least one of a change of a user associated with the slave device, a change of a wearing state of the slave device, a change of a connection state of the slave device, or a change of a power state of the slave device.

The electronic device according to various embodiments may be one of various types of electronic devices. The electronic devices may include, for example, a portable communication device (e.g., a smart phone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wired), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 340) including one or more instructions that are stored in a storage medium (e.g., internal memory 336 or external memory 338) that is readable by a machine (e.g., the electronic device 301). For example, a processor (e.g., the processor 320) of the machine (e.g., the electronic device 301) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:
a communication circuit; and
at least one processor configured to:
obtain first biometric information from a first audio output device using the communication circuit,
obtain second biometric information from a second audio output device using the communication circuit,
obtain third biometric information from an external electronic device using the communication circuit,
determine a master device among the first audio output device and the second audio output device based on a similarity between the first biometric information, the second biometric information and the third biometric information, and
control the first audio output device and the second audio output device using the master device.

2. The electronic device of claim 1, wherein the external electronic device is a wearable device worn by a user of the electronic device.

3. The electronic device of claim 1, wherein the at least one processor is further configured to:
determine the first audio output device as the master device when a first similarity between the first biometric information and the third biometric information is higher than a second similarity between the second biometric information and the third biometric information, and
determine the second audio output device as the master device when the second similarity is higher than the first similarity.

4. The electronic device of claim 1, wherein the at least one processor is further configured to:
in response to a notification event of the electronic device, provide a notification only to the master device among the first audio output device and the second audio output device.

5. The electronic device of claim 4, wherein the notification corresponds to a reception of an incoming call or a message by the electronic device.

6. The electronic device of claim 1, wherein each of the first biometric information, the second biometric information, and the third biometric information include at least one of a heart rate, a heartbeat waveform, a heartbeat timing, or a heartbeat frequency.

7. The electronic device of claim 1, wherein the at least one processor is further configured to:
obtain the third biometric information when a similarity between the first biometric information and the second biometric information is less than a first threshold.

8. The electronic device of claim 7, further comprising:
a display,
wherein the at least one processor is further configured to:
when the similarity is less than the first threshold, provide, on the display, a user interface for independently control the first audio output device and the second audio output device.

9. The electronic device of claim 8, wherein the at least one processor is further configured to:
when the similarity is less than the first threshold, provide, on the display, a first icon indicating that the first audio output device and the second audio output device are worn by different users, and when the similarity is equal to or greater than the first threshold, provide, on the display, a second icon indicating that the first audio output device and the second audio output device are worn by the same user.

10. The electronic device of claim 1, wherein the first biometric information, the second biometric information, and the third biometric information are obtained by the first audio output device, the second audio output device, and the external electronic device respectively.

11. A method for controlling audio output devices by an electronic device comprising:
 obtaining first biometric information from a first audio output device;
 obtaining second biometric information from a second audio output device;
 obtaining third biometric information from an external electronic device;
 determining a master device among the first audio output device and the second audio output device based on a similarity between the first biometric information, the second biometric information and the third biometric information; and
 controlling the first audio output device and the second audio output device using the master device.

12. The method of claim 11, wherein the external electronic device is a wearable device worn by a user of the electronic device.

13. The method of claim 11, wherein the determining of the master device comprises:
 determining the first audio output device as the master device when a first similarity between the first biometric information and the third biometric information is higher than a second similarity between the second biometric information and the third biometric information; and
 determining the second audio output device as the master device when the second similarity is higher than the first similarity.

14. The method of claim 11, further comprising:
 in response to a notification event of the electronic device, providing a notification only to the master device among the first audio output device and the second audio output device.

15. The method of claim 14, wherein the notification corresponds to a reception of an incoming call or a message by the electronic device.

16. The method of claim 11, wherein each of the first biometric information, the second biometric information, and the third biometric information include at least one of a heart rate, a heartbeat waveform, a heartbeat timing, or a heartbeat frequency.

17. The method of claim 11, wherein the obtaining of the third biometric information comprises,
 obtaining the third biometric information when a similarity between the first biometric information and the second biometric information is less than a first threshold.

18. The method of claim 17, further comprising:
 when the similarity is less than the first threshold, providing a user interface for independently control the first audio output device and the second audio output device.

19. The method of claim 18, further comprising:
 when the similarity is less than the first threshold, providing a first icon indicating that the first audio output device and the second audio output device are worn by different users; and
 when the similarity is equal to or greater than the first threshold, providing a second icon indicating that the first audio output device and the second audio output device are worn by the same user.

20. The method of claim 11, wherein the first biometric information, the second biometric information, and the third biometric information are obtained by the first audio output device, the second audio output device, and the external electronic device respectively.

* * * * *